United States Patent [19]
Whitney

[11] Patent Number: 5,928,888
[45] Date of Patent: Jul. 27, 1999

[54] METHODS AND COMPOSITIONS FOR SENSITIVE AND RAPID, FUNCTIONAL IDENTIFICATION OF GENOMIC POLYNUCLEOTIDES AND SECONDARY SCREENING CAPABILITIES

[75] Inventor: Michael A. Whitney, La Jolla, Calif.

[73] Assignee: Aurora Biosciences Corporation, San Diego, Calif.

[21] Appl. No.: 08/719,697

[22] Filed: Sep. 26, 1996

[51] Int. Cl.[6] .............. C12Q 1/02; C12Q 1/68; C12Q 1/00; G01N 33/566
[52] U.S. Cl. .............. 435/29; 435/4; 435/6; 435/455; 435/463; 435/69.1; 435/91.1; 435/230; 435/235; 436/501; 536/23.1; 536/24.3; 536/24.31; 536/24.5
[58] Field of Search .............. 435/4, 6, 29, 40.51, 435/69.1, 91.1, 69.8, 70.1, 172.1, 172.3, 195, 230, 231, 325, 968, 444, 455, 463, 464; 536/23.1, 24.3, 24.31, 24.5; 514/44; 436/501

[56] References Cited

U.S. PATENT DOCUMENTS

| | | |
|---|---|---|
| 4,935,363 | 6/1990 | Brown et al. . |
| 4,980,281 | 12/1990 | Housey . |
| 5,264,354 | 11/1993 | Solenberg . |
| 5,266,464 | 11/1993 | Housey . |
| 5,298,429 | 3/1994 | Evans et al. ............ 436/501 |
| 5,326,691 | 7/1994 | Hozier . |
| 5,354,674 | 10/1994 | Hodgson . |
| 5,364,783 | 11/1994 | Ruley et al. . |
| 5,378,603 | 1/1995 | Brown et al. . |
| 5,401,629 | 3/1995 | Harpold et al. . |
| 5,436,128 | 7/1995 | Harpold et al. . |
| 5,464,764 | 11/1995 | Capecchi et al. . |
| 5,474,897 | 12/1995 | Weiss et al. . |
| 5,487,992 | 1/1996 | Capecchi et al. . |
| 5,501,979 | 3/1996 | Geller et al. . |
| 5,514,561 | 5/1996 | Quante et al. ............ 435/18 |
| 5,569,588 | 10/1996 | Ashby et al. . |
| 5,580,722 | 12/1996 | Foulkes et al. . |
| 5,604,090 | 2/1997 | Alexander et al. . |
| 5,614,396 | 3/1997 | Bradley et al. . |
| 5,627,058 | 5/1997 | Ruley et al. . |
| 5,627,059 | 5/1997 | Capecchi et al. . |
| 5,631,153 | 5/1997 | Capecchi et al. . |
| 5,639,596 | 6/1997 | Bornkamm et al. . |
| 5,652,128 | 7/1997 | Jarvik . |
| 5,665,543 | 9/1997 | Foulkes et al. . |
| 5,741,657 | 4/1998 | Tsien et al. ............ 435/18 |
| 5,777,888 | 7/1998 | Rine et al. ............ 364/496 |

FOREIGN PATENT DOCUMENTS

| | | |
|---|---|---|
| 0 291 893 A1 | 5/1988 | European Pat. Off. . |
| 0 731 169 A1 | 9/1996 | European Pat. Off. . |
| WO 88/07579 | 10/1988 | WIPO . |
| WO 91/01379 | 2/1991 | WIPO . |
| WO 92/05286 | 4/1992 | WIPO . |
| WO 93/11257 | 6/1993 | WIPO . |
| WO 94/01137 | 1/1994 | WIPO . |
| WO 94/24301 | 2/1994 | WIPO . |
| WO 94/17208 | 8/1994 | WIPO . |
| WO 94/23039 | 10/1994 | WIPO . |
| WO 94/24301 | 10/1994 | WIPO . |
| WO 95/05601 | 2/1995 | WIPO . |
| WO 96/03647A1 | 2/1996 | WIPO . |
| WO 96/04557 | 2/1996 | WIPO . |
| WO 96/05511 | 2/1996 | WIPO . |
| WO 96/16179 | 5/1996 | WIPO . |
| WO 96/30540 | 10/1996 | WIPO . |
| WO 97/19180 | 5/1997 | WIPO . |
| WO 97/19183 | 5/1997 | WIPO . |

OTHER PUBLICATIONS

Fiering et al, "Improved FACS–gal: flow cytometric analysis and sorting of viable eukaryotic cells expressing reporter gene constructs", Cytometry 12:291–301 1991.
Bolker et al., Mol. Gen. Genet. 248:547–52 (1995).
Brenner et al., Proc. Natl. Acad. Sci. USA. 86:5517–5521 (1989).
Bush et al., Cell Calcium. 8:455–472 (1987).
Choi et al., Oncogne. 9:1261–1266 (1994).
Claes et al., Plant Journal. 1:15–26 (1991).
Cone et al., Proc. Natl. Acad. Sci. USA. 81:6349–6353 (1984).
Davis et al., J. Biol. Chem. 262:4075–4082 (1987).
Deursen et al., Proc. Natl. Acad. Sci. USA. 92:7376–7380 (1995).
Deutsch et al., Proc. Natl. Acad. Sci. USA. 85:7922–7926 (1988).
Ehrhardt et al., Cell. 856:673–681 (1996).
Fukushige et al., Proc. Natl. Acad. Sci. USA. 89–7905–7909 (1992).
Frohman et al., Cell 56:145–147 (1989).
Gogos et al., J. Cell Biol. 134:837–847 (1996).
Gould et al., Analyt. Biochem. 175:5–13 (1988).
Guild et al., J. Virology. 62:3795–3801 (1988).
Hoshizaki et al., Genome. 38:497–506 (1995).
Ioffe et al., Proc. Natl. Acad. Sci. USA. 92:7357–7361 (1995).
Kerr et al., Cold Spring Harbor Symposia on Quantitative Biology. 54:767–775 (1989).
Kuspa et al., Genetics. 138:665–674 (1994).
Kwiatkowski et al., Biochem. Biophys. Research Comm. 222:601–606 (1996).

(List continued on next page.)

*Primary Examiner*—Jeffrey Fredman
*Attorney, Agent, or Firm*—Fish & Richardson P.C.

[57] ABSTRACT

The invention provides for a methods and compositions for identifying proteins or compounds that directly or indirectly modulate a genomic polynucleotide and methods for identifying active genomic polynucleotides. Generally, the method comprises inserting a BL (beta-lactamase) expression construct into an eukaryotic genome, usually non-yeast, contained in at least one living cell, contacting the cell with a predetermined concentration of a modulator, and detecting BL activity in the cell.

45 Claims, 4 Drawing Sheets

OTHER PUBLICATIONS

Luo et al., Plant Journal. 1:59–69 (1991).

Miklos et al., Cell. 86:521–529 (1996).

Muzyczka et al., Current Topics in Microbiology and Immunology. 158:97–127 (1992).

Natarajan et al., Nucleic Acids Research. vol. 23 No. 19 (1995).

Nickoloff, J.A., Mol. Cell. Biol. 12:5311–5318 (1992).

Obermeyer et al., Euro. J. Cell Biol. 56:319–321 (1991).

Otani et al., J. Biol. Chem. 263:7322–7329 (1988).

Pennisi et al., Science. 272:1736–1738 (1996).

Pierson et al., Dev. Biol. 174:160–173 (1996).

Rathore et al., Dev. Biol. 148:612–619 (1991).

Renkens et al., Mol. Gen. Genet. 233:53–64 (1992).

Rich, I., Blood. 86:463–472 (1995).

Rijkers et al., Biochim. Biophys. Acta. 1307:294–300 (1996).

Serafini et al., Immunity, 3:239–250 (1995).

Siekevitz et al., Proc. Natl. Acad. Sci. USA. 84:5389–5393 (1987).

Skarnes et al., Current Opinion in Biotechnology. 4:684–689 (1993).

Soriano et al., J. of Virology. 65:2314–2319 (1991).

Topping er al., Plant Journal. 5:895–903 (1994).

Vidal et al., J. Leukocyte Biol. 58:382–390 (1995).

Yeh et al., Proc. Natl. Acad. Sci. USA. 92:7036–7040 (1995).

Zmuidzinas et al., EMBO Journal. 14:1–11 (1995).

Tadros et al., Synthesis of quinoline derivatives., *Indian Journal of Chemistry.*, 14B:467–469 (Jun. 1976).

Cartwright et al., "Efficient Secretion in Yeast Based on Fragments from $K_1$ Killer Preprotoxin", *Yeast*, vol. 8, 261–272 (1992).

Kadonaga et al., "The Role of the β–Lactamase Signal Sequence in the Secretion of Proteins by *Escherichia coli*," *The Journal of Biological Chemistry*, vol. 259, No. 4, Feb. 25, 1984, pp. 2149–2154.

Sekkali et al., "A comparative study of reporter gene activities in fish cells and embryos", *Molecular Marine Biology and Biotechnology* (1994) 3(1)30–34.

Wong et al., "Appearance of β–lactamas activity in animal cells upon liposome–mediated gene transfer", *Gene*, 10 (1980) 87–94.

Brenner et al., Analysis of mammalian cell genetic regulation in situ by using retrovirus–derived "portable exons" carrying the *Escherichia coli* lac Z gene, *Proc. Natl. Acad. Sci. U.S.A.* 86:5517–5521 (1989).

Dougherty and Temin, A promoterless retroviral vector indicates that there are sequences in U3 required for 3' RNA processing, *Proc. Natl. Acad. Sci. U.S.A.* 84:1197–1201 (1987).

Hamada, Activation of an enhancerless gene by chromosomal integration,*Mol. Cell. Biol.* 6:4179–4184 (1986).

Hiller et al., Insertional activation of a promoterless thymidine kinase gene, *Mol. Cell Biol.* 8:3298–3302 (1988).

Nakajima et al., An improved retroviral vector for assaying promoter activity, analysis of promoter interference in pIP211 vector*FEBS* 315:129–133 (1993).

Soriano et al., Petroviruses and insertional mutagenesis in mice:proviral integration at the Mov 34 locus leads to early embryonic death *Genes & Development* 1:366–375 (1987).

Yu et al., Self–inactivating retroviral vectors designed for transfer of whole genes into mammalian cells,*Proc. Natl. Acad. Sci. U.S.A.* 83:3194–3198 (1986).

Boss, Valerie, "Induction of NFAT–mediated Transcription by Gq–coupled Receptors in Lymphoid and Non–Lymphoid Cells," *The Journal of Biological Chemistry*, May 3, 1996, vol. 271, No. 18, pp. 10429–10432.

Mattila, Petri S., "The actions of cyclosporin A and FK506 suggest a novel step in the activation of T lymphocytes," *The EMBO Journal*, 1990, vol. 9, No. 13, pp. 4425–4433.

Skarnes et al., A gene trap approach in mouse embryonic stem cells: the lacZ reporter is activated by splicing, reflects endogenous gene expression, and is mutagenic in mice, *Genes & Development*, 6:903–918 (1992).

Colbere–Garapin et al., "Patterns of integration of exogenous DNA sequences transfected into mammalian cells of primate and rodent origin", *Gene*, 50 (1986) 279–288.

Rouet et al., "Introduction of Double–Strand Breaks into the Genome of Mouse Cells by Expression of a Rare–Cutting Endonuclease," *Molecular and Cellular Biology*, Dec. 1994, pp. 8096–8106.

Natarajan et al., "A lacZ hygromycin fusion gene and its use in a gene trap vector for marking embryonic stem cells," *Nucleic Acids Research*, 1995, vol. 23, No. 19, pp. 4003–4004.

Reddy et al., Developmental Biology, "Fluorescence–activated sorting of totipotent embryonic stem cells expressing developmentally regulated lacZ fusion genes," *Proc. Natl. Acad. Sci.*, USA, vol. 89, pp. 6721–6725.

Mountford et al., Development Biology, "Dicistronic targeting constructs: Reporters and modifiers of mammalian gene expression," *Proc. Natl. Acad. Sci.*, USA, vol. 91, pp. 4303–4307, May 1994.

Bolker et al., Original paper, Communicated by C.A.M.J.J. van den Hondel, "Tagging pathogenicity genes in Ustilago maydis by restriction enzyme–mediated integration," (REMI), undated.

Gossler et al., "Mouse Embryonic Stem Cells and Reporter Constructs to Detect Developmentally Regulated Genes," *Reports*, Apr. 28, 1989.

Wurst et al., "A Large–Scale Gene–Trap Screen for Insertional Mutations in Developmentally Regulated Genes in Mice," *Genetics*, Feb. 1995, vol. 139, pp. 889–899.

Mountford et al., "Internal ribosome entry sites and dicistronic RNAs in mammalian transgenesis," *Tig*, May 1995, vol. 11.

Mosser et al., "Use of a Dicistronic Expression Cassette Encoding the Green Fluorescent Protein for the Screening and Selection of Cells Expressing Inducible Gene Products," *Research Reports. BioTechniques*, Jan. 1997, vol. 22, pp. 150–161.

Debenham et al., "The effect of X–rays and ultraviolet light on DAN–mediated gene transfer in mammalian cells," *Int. J. Radiat. Biol.*, 1984, vol. 46, No. 5, pp. 555–568.

Cone et al., "High–efficiency gene transfer into mammalian cells: Generation of helper–free recombinant retrovirus with broad mammalian host range," *Proc. Natl. Acad. Sci*, USA, Oct. 1974, vol. 81, pp. 6349–6353.

von Melchner et al., "Identification of Cellular Promoters by Using a Retrovirus Promoter Trap," *Journal of Virology*, Aug. 1989, pp. 3227–3233.

Kronenberg, "Radiation–induced genomic instability," *Int. J. Radiat. Biol.*, vol. 66, No. 5, pp. 603–609.

Yoshida et al., "A new strategy of gene trapping in ES cells using 3' Race," *Transgenic Research*, 1995, vol. 4, pp. 277–287.

Skarnes et al., "Capturing genes encoding membranes and secreted proteins important for mouse development," *Proc. Natl. Acad. Sci.,* USA, Developmental Biology, Jul. 1995, vol. 92, pp. 6592–6596.

Godwin et al., "Spontaneous and restriction enzyme–induced chromosomal recombination in mammalian cells," *Proc. Natl. Acad. Sci.,* USA, Genetics, Dec. 1994, vol. 91, pp. 12554–12558.

Hoshizaki et al., "Identification of fat–cell enhancer activity in *Drosophila melanogaster* using P–element enhancer traps," *Genome,* 1995, vol. 38, pp. 1497–1506.

Okazaki et al., "A Novel Nuclear Protein with Zing Fingers Down–regulated during Early Mammalian Cell Differentiation," *The Journal of Biological Chemistry,* Mar. 4, 1994, vol. 629, No. 9, pp. 6900–6907.

Reid et al., "Cotransformation and Gene Targeting in Mouse Embryonic Stem Cells," *Molecular and Cellular Biology,* May 1991, vol. 11, No. 5, pp. 2769–2777.

Potocnik et al., "In vitro generation of lymphoid precursors from embryonic stem cells," *The EMBO Journal,* 1994, vol. 13, No. 22, pp. 5274–5283.

Palacio et al., "In vitro generation of hematopoietic stem cells from an embryonic stem cell line," *Proc. Natl. Acad. Sci.,* Developmental Biology, Aug. 1995, vol. 92, pp. 7530–7534.

Shapiro et al., "RNA splice junctions of different classes of eukaryotes: sequence statistics and functional implications in gene expression." *Nucleic Acids Research,* 1987, vol. 15, No. 17.

Friedrich et al., "Promoter traps in embryonic stem cells: a genetic screen to identify and mutate developmental genes in mice," *Genes & Development,* vol. 5, pp. 1513–1523 (1991).

Niwa et al., "An Efficient Gene–Trap Method Using Poly A Trap Vectors and Characterization of Gene–Trap Events," *J. Biochem.,* 1993, vol. 113, pp. 343–349.

Toyoda et al., "An enhanced promoter trap protocol," *Mammalian Geome,* 1995, vol. 6, pp. 426–428.

Kuspa et al., "Tagging developmental genes in *Dictyostelium* by restriction enzyme–mediated integration of plasmid DNA," *Proc. Natl. Acad. Sci.,* USA, 1992.

Jarvik et al., "CD–Tagging: A New Approach to Gene and Protein Discovery and Analysis," *Research Reports, Biotechniques,* May 1996, vol. 20, pp. 896–904.

Nickoloff, "Transcription Enhances Intrachromosomal Homologous Recombination in Mammalian Cells," *Molecular and Cellular Biology,* Dec. 1992, vol. 12, No. 12, pp. 5311–5318.

Friedrich et al., "Insertional Mutagenesis by Retroviruses and Promoter Traps in Embryonic Stem Cells," *Methods in Enzymology,* vol. 225, pp. 681–701.

Hill et al., "Screening for Novel Pattern Formation Genes Using Gene Trap Approaches," *Methods in Enzymology,* vol. 225, pp. 661–679.

Townley et al., "Rapid sequence analysis of gene trap integrations to generate a resource of insertional mutations in mice," *Genome Res.,* Mar. 1997, vol. 7, No. 3, pp. 293–298.

Gogos et al., "Gene trapping in differentiating cell lines: regulation of the lysosomal protease cathepsin B in skeletal myoblast growth and fusion," *J. Cell. Biol.,* Aug. 1996, vol. 134, No. 4, pp. 837–847.

Forrester et al., "An induction gene trap screen in embryonic stem cells: Identification of genes that respond to retinoic acid in vitro", *Proc. Natl. Acad. Sci.,* USA, Feb. 1996, vol. 93, pp. 1677–1682.

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 795 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 1..795

(xi) SEQUENCE DESCRIPTION: SEQ ID NO:1:

```
ATG AGT CAC CCA GAA ACG CTG GTG AAA GTA AAA GAT GCT GAA GAT CAG      48
Met Ser His Pro Glu Thr Leu Val Lys Val Lys Asp Ala Glu Asp Gln
  1               5                  10                  15

TTG GGT GCA CGA GTG GGT TAC ATC GAA CTG GAT CTC AAC AGC GGT AAG      96
Leu Gly Ala Arg Val Gly Tyr Ile Glu Leu Asp Leu Asn Ser Gly Lys
             20                  25                  30
```

| | |
|---|---|
| ATC CTT GAG AGT TTT CGC CCC GAA GAA CGT TTT CCA ATG ATG AGC ACT<br>Ile Leu Glu Ser Phe Arg Pro Glu Glu Arg Phe Pro Met Met Ser Thr<br>35                     40                        45 | 144 |
| TTT AAA GTT CTG CTA TGT GGC GCG GTA TTA TCC CGT GTT GAC GCC GGG<br>Phe Lys Val Leu Leu Cys Gly Ala Val Leu Ser Arg Val Asp Ala Gly<br>50                     55                        60 | 192 |
| CAA GAG CAA CTC GGT CGC CGC ATA CAC TAT TCT CAG AAT GAC TTG GTT<br>Gln Glu Gln Leu Gly Arg Arg Ile His Tyr Ser Gln Asn Asp Leu Val<br>65                     70                      75                        80 | 240 |
| GAG TAC TCA CCA GTC ACA GAA AAG CAT CTT ACG GAT GGC ATG ACA GTA<br>Glu Tyr Ser Pro Val Thr Glu Lys His Leu Thr Asp Gly Met Thr Val<br>                     85                        90                        95 | 288 |
| AGA GAA TTA TGC AGT GCT GCC ATA ACC ATG AGT GAT AAC ACT GCG GCC<br>Arg Glu Leu Cys Ser Ala Ala Ile Thr Met Ser Asp Asn Thr Ala Ala<br>                100                       105                     110 | 336 |
| AAC TTA CTT CTG ACA ACG ATC GGA GGA CCG AAG GAG CTA ACC GCT TTT<br>Asn Leu Leu Leu Thr Thr Ile Gly Gly Pro Lys Glu Leu Thr Ala Phe<br>                115                       120                     125 | 384 |
| TTG CAC AAC ATG GGG GAT CAT GTA ACT CGC CTT GAT CGT TGG GAA CCG<br>Leu His Asn Met Gly Asp His Val Thr Arg Leu Asp Arg Trp Glu Pro<br>130                        135                       140 | 432 |
| GAG CTG AAT GAA GCC ATA CCA AAC GAC GAG CGT GAC ACC ACG ATG CCT<br>Glu Leu Asn Glu Ala Ile Pro Asn Asp Glu Arg Asp Thr Thr Met Pro<br>145                        150                       155                     160 | 480 |
| GCA GCA ATG GCA ACA ACG TTG CGC AAA CTA TTA ACT GGC GAA CTA CTT<br>Ala Ala Met Ala Thr Thr Leu Arg Lys Leu Leu Thr Gly Glu Leu Leu<br>                165                       170                     175 | 528 |
| ACT CTA GCT TCC CGG CAA CAA TTA ATA GAC TGG ATG GAG GCG GAT AAA<br>Thr Leu Ala Ser Arg Gln Gln Leu Ile Asp Trp Met Glu Ala Asp Lys<br>                180                       185                     190 | 576 |
| GTT GCA GGA CCA CTT CTG CGC TCG GCC CTT CCG GCT GGC TGG TTT ATT<br>Val Ala Gly Pro Leu Leu Arg Ser Ala Leu Pro Ala Gly Trp Phe Ile<br>                195                       200                     205 | 624 |
| GCT GAT AAA TCT GGA GCC GGT GAG CGT GGG TCT CGC GGT ATC ATT GCA<br>Ala Asp Lys Ser Gly Ala Gly Glu Arg Gly Ser Arg Gly Ile Ile Ala<br>210                        215                       220 | 672 |
| GCA CTG GGG CCA GAT GGT AAG CCC TCC CGT ATC GTA GTT ATC TAC ACG<br>Ala Leu Gly Pro Asp Gly Lys Pro Ser Arg Ile Val Val Ile Tyr Thr<br>225                        230                       235                     240 | 720 |
| ACG GGG AGT CAG GCA ACT ATG GAT GAA CGA AAT AGA CAG ATC GCT GAG<br>Thr Gly Ser Gln Ala Thr Met Asp Glu Arg Asn Arg Gln Ile Ala Glu<br>                245                       250                     255 | 768 |
| ATA GGT GCC TCA CTG ATT AAG CAT TGG<br>Ile Gly Ala Ser Leu Ile Lys His Trp<br>260                        265 | 795 |

(2) INFORMATION FOR SEQ ID NO:2:

(i) SEQUENCE CHARACTERISTICS:
        (A) LENGTH: 265 amino acids
        (B) TYPE: amino acid
        (D) TOPOLOGY: linear (ii) MOLECULE TYPE: protein (xi) SEQUENCE DESCRIPTION: SEQ ID NO:2:

Met Ser His Pro Glu Thr Leu Val Lys Val Lys Asp Ala Glu Asp Gln
1                   5                   10                 15

Leu Gly Ala Arg Val Gly Tyr Ile Glu Leu Asp Leu Asn Ser Gly Lys
                 20                   25                   30

Ile Leu Glu Ser Phe Arg Pro Glu Glu Arg Phe Pro Met Met Ser Thr
                 35                   40                   45

```
Phe Lys Val Leu Leu Cys Gly Ala Val Leu Ser Arg Val Asp Ala Gly
    50                  55                  60

Gln Glu Gln Leu Gly Arg Arg Ile His Tyr Ser Gln Asn Asp Leu Val
65              70                  75                  80

Glu Tyr Ser Pro Val Thr Glu Lys His Leu Thr Asp Gly Met Thr Val
                85                  90                  95

Arg Glu Leu Cys Ser Ala Ala Ile Thr Met Ser Asp Asn Thr Ala Ala
                100                 105                 110

Asn Leu Leu Leu Thr Thr Ile Gly Gly Pro Lys Glu Leu Thr Ala Phe
            115                 120                 125

Leu His Asn Met Gly Asp His Val Thr Arg Leu Asp Arg Trp Glu Pro
    130                 135                 140

Glu Leu Asn Glu Ala Ile Pro Asn Asp Glu Arg Asp Thr Thr Met Pro
145                 150                 155                 160

Ala Ala Met Ala Thr Thr Leu Arg Lys Leu Leu Thr Gly Glu Leu Leu
                165                 170                 175

Thr Leu Ala Ser Arg Gln Gln Leu Ile Asp Trp Met Glu Ala Asp Lys
            180                 185                 190

Val Ala Gly Pro Leu Leu Arg Ser Ala Leu Pro Ala Gly Trp Phe Ile
        195                 200                 205

Ala Asp Lys Ser Gly Ala Gly Glu Arg Gly Ser Arg Gly Ile Ile Ala
    210                 215                 220

Ala Leu Gly Pro Asp Gly Lys Pro Ser Arg Ile Val Val Ile Tyr Thr
225                 230                 235                 240

Thr Gly Ser Gln Ala Thr Met Asp Glu Arg Asn Arg Gln Ile Ala Glu
                245                 250                 255

Ile Gly Ala Ser Leu Ile Lys His Trp
                260                 265

(2) INFORMATION FOR SEQ ID NO:3:

(i) SEQUENCE CHARACTERISTICS:
        (A) LENGTH: 858 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..858

(xi) SEQUENCE DESCRIPTION: SEQ ID NO:3:

ATG AGA ATT CAA CAT TTC CGT GTC GCC CTT ATT CCC TTT TTT GCG GCA        48
Met Arg Ile Gln His Phe Arg Val Ala Leu Ile Pro Phe Phe Ala Ala
            270                 275                 280

TTT TGC CTT CCT GTT TTT GGT CAC CCA GAA ACG CTG GTG AAA GTA AAA        96
Phe Cys Leu Pro Val Phe Gly His Pro Glu Thr Leu Val Lys Val Lys
            285                 290                 295

GAT GCT GAA GAT CAG TTG GGT GCA CGA GTG GGT TAC ATC GAA CTG GAT       144
Asp Ala Glu Asp Gln Leu Gly Ala Arg Val Gly Tyr Ile Glu Leu Asp
        300                 305                 310

CTC AAC AGC GGT AAG ATC CTT GAG AGT TTT CGC CCC GAA GAA CGT TTT       192
Leu Asn Ser Gly Lys Ile Leu Glu Ser Phe Arg Pro Glu Glu Arg Phe
    315                 320                 325

CCA ATG ATG AGC ACT TTT AAA GTT CTG CTA TGT GGC GCG GTA TTA TCC       240
Pro Met Met Ser Thr Phe Lys Val Leu Leu Cys Gly Ala Val Leu Ser
330                 335                 340                 345

CGT GTT GAC GCC GGG CAA GAG CAA CTC GGT CGC CGC ATA CAC TAT TCT       288
Arg Val Asp Ala Gly Gln Glu Gln Leu Gly Arg Arg Ile His Tyr Ser
```

```
                        350                 355                 360
CAG AAT GAC TTG GTT GAG TAC TCA CCA GTC ACA GAA AAG CAT CTT ACG         336
Gln Asn Asp Leu Val Glu Tyr Ser Pro Val Thr Glu Lys His Leu Thr
                365                 370                 375

GAT GGC ATG ACA GTA AGA GAA TTA TGC AGT GCT GCA ATA ACC ATG AGT         384
Asp Gly Met Thr Val Arg Glu Leu Cys Ser Ala Ala Ile Thr Met Ser
            380                 385                 390

GAT AAC ACT GCG GCC AAC TTA CTT CTG ACA ACG ATC GGA GGA CCG AAG         432
Asp Asn Thr Ala Ala Asn Leu Leu Leu Thr Thr Ile Gly Gly Pro Lys
        395                 400                 405

GAG CTA ACC GCT TTT TTG CAC AAC ATG GGG GAT CAT GTA ACT CGC CTT         480
Glu Leu Thr Ala Phe Leu His Asn Met Gly Asp His Val Thr Arg Leu
410                 415                 420                 425

GAT CGT TGG GAA CCG GAG CTG AAT GAA GCC ATA CCA AAC GAC GAG CGT         528
Asp Arg Trp Glu Pro Glu Leu Asn Glu Ala Ile Pro Asn Asp Glu Arg
                430                 435                 440

GAC ACC ACG ATG CCT GCA GCA ATG GCA ACA ACG TTG CGC AAA CTA TTA         576
Asp Thr Thr Met Pro Ala Ala Met Ala Thr Thr Leu Arg Lys Leu Leu
            445                 450                 455

ACT GGC GAA CTA CTT ACT CTA GCT TCC CGG CAA CAA TTA ATA GAC TGG         624
Thr Gly Glu Leu Leu Thr Leu Ala Ser Arg Gln Gln Leu Ile Asp Trp
        460                 465                 470

ATG GAG GCG GAT AAA GTT GCA GGA CCA CTT CTG CGC TCG GCC CTT CCG         672
Met Glu Ala Asp Lys Val Ala Gly Pro Leu Leu Arg Ser Ala Leu Pro
475                 480                 485

GCT GGC TGG TTT ATT GCT GAT AAA TCT GGA GCC GGT GAG CGT GGG TCT         720
Ala Gly Trp Phe Ile Ala Asp Lys Ser Gly Ala Gly Glu Arg Gly Ser
                490                 495                 500                 505

CGC GGT ATC ATT GCA GCA CTG GGG CCA GAT GGT AAG CCC TCC CGT ATC         768
Arg Gly Ile Ile Ala Ala Leu Gly Pro Asp Gly Lys Pro Ser Arg Ile
            510                 515                 520

GTA GTT ATC TAC ACG ACG GGG AGT CAG GCA ACT ATG GAT GAA CGA AAT         816
Val Val Ile Tyr Thr Thr Gly Ser Gln Ala Thr Met Asp Glu Arg Asn
        525                 530                 535

AGA CAG ATC GCT GAG ATA GGT GCC TCA CTG ATT AAG CAT TGG                 858
Arg Gln Ile Ala Glu Ile Gly Ala Ser Leu Ile Lys His Trp
    540                 545                 550

(2) INFORMATION FOR SEQ ID NO:4:

(i) SEQUENCE CHARACTERISTICS:
        (A) LENGTH: 286 amino acids
        (B) TYPE: amino acid
        (D) TOPOLOGY: linear (ii) MOLECULE TYPE: protein (xi) SEQUENCE DESCRIPTION: SEQ ID NO:4:

Met Arg Ile Gln His Phe Arg Val Ala Leu Ile Pro Phe Phe Ala Ala
 1               5                  10                  15

Phe Cys Leu Pro Val Phe Gly His Pro Glu Thr Leu Val Lys Val Lys
                20                  25                  30

Asp Ala Glu Asp Gln Leu Gly Ala Arg Val Gly Tyr Ile Glu Leu Asp
            35                  40                  45

Leu Asn Ser Gly Lys Ile Leu Glu Ser Phe Arg Pro Glu Glu Arg Phe
        50                  55                  60

Pro Met Met Ser Thr Phe Lys Val Leu Leu Cys Gly Ala Val Leu Ser
65                  70                  75                  80

Arg Val Asp Ala Gly Gln Glu Gln Leu Gly Arg Arg Ile His Tyr Ser
                85                  90                  95
```

```
        Gln Asn Asp Leu Val Glu Tyr Ser Pro Val Thr Glu Lys His Leu Thr
                100                 105                 110

Asp Gly Met Thr Val Arg Glu Leu Cys Ser Ala Ala Ile Thr Met Ser
                    115                 120                 125

Asp Asn Thr Ala Ala Asn Leu Leu Thr Thr Ile Gly Gly Pro Lys
                130                 135                 140

Glu Leu Thr Ala Phe Leu His Asn Met Gly Asp His Val Thr Arg Leu
        145                 150                 155                 160

Asp Arg Trp Glu Pro Glu Leu Asn Glu Ala Ile Pro Asn Asp Glu Arg
                        165                 170                 175

Asp Thr Thr Met Pro Ala Ala Met Ala Thr Leu Arg Lys Leu Leu
                    180                 185                 190

Thr Gly Glu Leu Leu Thr Leu Ala Ser Arg Gln Gln Leu Ile Asp Trp
                195                 200                 205

Met Glu Ala Asp Lys Val Ala Gly Pro Leu Leu Arg Ser Ala Leu Pro
            210                 215                 220

Ala Gly Trp Phe Ile Ala Asp Lys Ser Gly Ala Gly Glu Arg Gly Ser
        225                 230                 235                 240

Arg Gly Ile Ile Ala Ala Leu Gly Pro Asp Gly Lys Pro Ser Arg Ile
                        245                 250                 255

Val Val Ile Tyr Thr Thr Gly Ser Gln Ala Thr Met Asp Glu Arg Asn
                    260                 265                 270

Arg Gln Ile Ala Glu Ile Gly Ala Ser Leu Ile Lys His Trp
                275                 280                 285

(2) INFORMATION FOR SEQ ID NO:5:

(i) SEQUENCE CHARACTERISTICS:
        (A) LENGTH: 843 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 49..843

(xi) SEQUENCE DESCRIPTION: SEQ ID NO:5:

AAGCTTTTTG CAGAAGCTCA GAATAAACGC AACTTTCCGG GTACCACC ATG GGG CAC              57
                                                    Met Gly His

CCA GAA ACG CTG GTG AAA GTA AAA GAT GCT GAA GAT CAG TTG GGT GCA             105
Pro Glu Thr Leu Val Lys Val Lys Asp Ala Glu Asp Gln Leu Gly Ala
290                 295                 300                 305

CGA GTG GGT TAC ATC GAA CTG GAT CTC AAC AGC GGT AAG ATC CTT GAG             153
Arg Val Gly Tyr Ile Glu Leu Asp Leu Asn Ser Gly Lys Ile Leu Glu
                310                 315                 320

AGT TTT CGC CCC GAA GAA CGT TTT CCA ATG ATG AGC ACT TTT AAA GTT             201
Ser Phe Arg Pro Glu Glu Arg Phe Pro Met Met Ser Thr Phe Lys Val
            325                 330                 335

CTG CTA TGT GGC GCG GTA TTA TCC CGT GAT GAC GCC GGG CAA GAG CAA             249
Leu Leu Cys Gly Ala Val Leu Ser Arg Asp Asp Ala Gly Gln Glu Gln
        340                 345                 350

CTC GGT CGC CGC ATA CAC TAT TCT CAG AAT GAC TTG GTT GAG TAC TCA             297
Leu Gly Arg Arg Ile His Tyr Ser Gln Asn Asp Leu Val Glu Tyr Ser
    355                 360                 365

CCA GTC ACA GAA AAG CAT CTT ACG GAT GGC ATG ACA GTA AGA GAA TTA             345
Pro Val Thr Glu Lys His Leu Thr Asp Gly Met Thr Val Arg Glu Leu
370                 375                 380                 385

TGC AGT GCT GCC ATA ACC ATG AGT GAT AAC ACT GCG GCC AAC TTA CTT             393
Cys Ser Ala Ala Ile Thr Met Ser Asp Asn Thr Ala Ala Asn Leu Leu
```

```
                    390              395             400
CTG ACA ACG ATC GGA GGA CCG AAG GAG CTA ACC GCT TTT TTG CAC AAC    441
Leu Thr Thr Ile Gly Gly Pro Lys Glu Leu Thr Ala Phe Leu His Asn
                405              410             415

ATG GGG GAT CAT GTA ACT CGC CTT GAT CAT TGG GAA CCG GAG CTG AAT    489
Met Gly Asp His Val Thr Arg Leu Asp His Trp Glu Pro Glu Leu Asn
            420              425             430

GAA GCC ATA CCA AAC GAC GAG CGT GAC ACC ACG ATG CCT GTA GCA ATG    537
Glu Ala Ile Pro Asn Asp Glu Arg Asp Thr Thr Met Pro Val Ala Met
        435              440             445

GCA ACA ACG TTG CGC AAA CTA TTA ACT GGC GAA CTA CTT ACT CTA GCT    585
Ala Thr Thr Leu Arg Lys Leu Leu Thr Gly Glu Leu Leu Thr Leu Ala
450             455              460             465

TCC CGG CAA CAA TTA ATA GAC TGG ATG GAG GCG GAT AAA GTT GCA GGA    633
Ser Arg Gln Gln Leu Ile Asp Trp Met Glu Ala Asp Lys Val Ala Gly
            470              475             480

CCA CTT CTG CGC TCG GCC CTT CCG GCT GGC TGG TTT ATT GCT GAT AAA    681
Pro Leu Leu Arg Ser Ala Leu Pro Ala Gly Trp Phe Ile Ala Asp Lys
        485              490             495

TCT GGA GCC GGT GAG CGT GGG TCT CGC GGT ATC ATT GCA GCA CTG GGG    729
Ser Gly Ala Gly Glu Arg Gly Ser Arg Gly Ile Ile Ala Ala Leu Gly
            500              505             510

CCA GAT GGT AAG CCC TCC CGT ATC GTA GTT ATC TAC ACG ACG GGG AGT    777
Pro Asp Gly Lys Pro Ser Arg Ile Val Val Ile Tyr Thr Thr Gly Ser
515             520              525

CAG GCA ACT ATG GAT GAA CGA AAT AGA CAG ATC GCT GAG ATA GGT GCC    825
Gln Ala Thr Met Asp Glu Arg Asn Arg Gln Ile Ala Glu Ile Gly Ala
530             535              540             545

TCA CTG ATT AAG CAT TGG                                            843
Ser Leu Ile Lys His Trp
                550

(2) INFORMATION FOR SEQ ID NO:6:

(i) SEQUENCE CHARACTERISTICS:
        (A) LENGTH: 265 amino acids
        (B) TYPE: amino acid
        (D) TOPOLOGY: linear (ii) MOLECULE TYPE: protein (xi) SEQUENCE DESCRIPTION: SEQ ID NO:6:

Met Gly His Pro Glu Thr Leu Val Lys Val Lys Asp Ala Glu Asp Gln
 1               5                  10                  15

Leu Gly Ala Arg Val Gly Tyr Ile Glu Leu Asp Leu Asn Ser Gly Lys
                20                  25                  30

Ile Leu Glu Ser Phe Arg Pro Glu Glu Arg Phe Pro Met Met Ser Thr
            35                  40                  45

Phe Lys Val Leu Leu Cys Gly Ala Val Leu Ser Arg Asp Asp Ala Gly
        50                  55                  60

Gln Glu Gln Leu Gly Arg Arg Ile His Tyr Ser Gln Asn Asp Leu Val
65                  70                  75                  80

Glu Tyr Ser Pro Val Thr Glu Lys His Leu Thr Asp Gly Met Thr Val
                85                  90                  95

Arg Glu Leu Cys Ser Ala Ala Ile Thr Met Ser Asp Asn Thr Ala Ala
            100                 105                 110

Asn Leu Leu Leu Thr Thr Ile Gly Gly Pro Lys Glu Leu Thr Ala Phe
        115                 120                 125

Leu His Asn Met Gly Asp His Val Thr Arg Leu Asp His Trp Glu Pro
    130                 135                 140
```

```
Glu Leu Asn Glu Ala Ile Pro Asn Asp Glu Arg Asp Thr Thr Met Pro
145                 150                 155                 160

Val Ala Met Ala Thr Thr Leu Arg Lys Leu Leu Thr Gly Glu Leu Leu
            165                 170                 175

Thr Leu Ala Ser Arg Gln Gln Leu Ile Asp Trp Met Glu Ala Asp Lys
            180                 185                 190

Val Ala Gly Pro Leu Leu Arg Ser Ala Leu Pro Ala Gly Trp Phe Ile
            195                 200                 205

Ala Asp Lys Ser Gly Ala Gly Glu Arg Gly Ser Arg Gly Ile Ile Ala
            210                 215                 220

Ala Leu Gly Pro Asp Gly Lys Pro Ser Arg Ile Val Ile Tyr Thr
225                 230                 235                 240

Thr Gly Ser Gln Ala Thr Met Asp Glu Arg Asn Arg Gln Ile Ala Glu
            245                 250                 255

Ile Gly Ala Ser Leu Ile Lys His Trp
            260                 265

(2) INFORMATION FOR SEQ ID NO:7:

(i) SEQUENCE CHARACTERISTICS:
        (A) LENGTH: 792 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..792

(xi) SEQUENCE DESCRIPTION: SEQ ID NO:7:

ATG GAC CCA GAA ACG CTG GTG AAA GTA AAA GAT GCT GAA GAT CAG TTG          48
Met Asp Pro Glu Thr Leu Val Lys Val Lys Asp Ala Glu Asp Gln Leu
                270                 275                 280

GGT GCA CGA GTG GGT TAC ATC GAA CTG GAT CTC AAC AGC GGT AAG ATC          96
Gly Ala Arg Val Gly Tyr Ile Glu Leu Asp Leu Asn Ser Gly Lys Ile
            285                 290                 295

CTT GAG AGT TTT CGC CCC GAA GAA CGT TTT CCA ATG ATG AGC ACT TTT         144
Leu Glu Ser Phe Arg Pro Glu Glu Arg Phe Pro Met Met Ser Thr Phe
            300                 305                 310

AAA GTT CTG CTA TGT GGC GCG GTA TTA TCC CGT ATT GAC GCC GGG CAA         192
Lys Val Leu Leu Cys Gly Ala Val Leu Ser Arg Ile Asp Ala Gly Gln
315                 320                 325

GAG CAA CTC GGT CGC CGC ATA CAC TAT TCT CAG AAT GAC TTG GTT GAG         240
Glu Gln Leu Gly Arg Arg Ile His Tyr Ser Gln Asn Asp Leu Val Glu
330                 335                 340                 345

TAC TCA CCA GTC ACA GAA AAG CAT CTT ACG GAT GGC ATG ACA GTA AGA         288
Tyr Ser Pro Val Thr Glu Lys His Leu Thr Asp Gly Met Thr Val Arg
            350                 355                 360

GAA TTA TGC AGT GCT GCC ATA ACC ATG AGT GAT AAC ACT GCG GCC AAC         336
Glu Leu Cys Ser Ala Ala Ile Thr Met Ser Asp Asn Thr Ala Ala Asn
            365                 370                 375

TTA CTT CTG ACA ACG ATC GGA GGA CCG AAG GAG CTA ACC GCT TTT TTG         384
Leu Leu Leu Thr Thr Ile Gly Gly Pro Lys Glu Leu Thr Ala Phe Leu
            380                 385                 390

CAC AAC ATG GGG GAT CAT GTA ACT CGC CTT GAT CAT TGG GAA CCG GAG         432
His Asn Met Gly Asp His Val Thr Arg Leu Asp His Trp Glu Pro Glu
            395                 400                 405

CTG AAT GAA GCC ATA CCA AAC GAC GAG CGT GAC ACC ACG ATG CCT GTA         480
Leu Asn Glu Ala Ile Pro Asn Asp Glu Arg Asp Thr Thr Met Pro Val
410                 415                 420                 425
```

-continued

```
GCA ATG GCA ACA ACG TTG CGC AAA CTA TTA ACT GGC GAA CTA CTT ACT       528
Ala Met Ala Thr Thr Leu Arg Lys Leu Leu Thr Gly Glu Leu Leu Thr
            430                 435                 440

CTA GCT TCC CGG CAA CAA TTA ATA GAC TGG ATG GAG GCG GAT AAA GTT       576
Leu Ala Ser Arg Gln Gln Leu Ile Asp Trp Met Glu Ala Asp Lys Val
                445                 450                 455

GCA GGA CCA CTT CTG CGC TCG GCC CTT CCG GCT GGC TGG TTT ATT GCT       624
Ala Gly Pro Leu Leu Arg Ser Ala Leu Pro Ala Gly Trp Phe Ile Ala
            460                 465                 470

GAT AAA TCT GGA GCC GGT GAG CGT GGG TCT CGC GGT ATC ATT GCA GCA       672
Asp Lys Ser Gly Ala Gly Glu Arg Gly Ser Arg Gly Ile Ile Ala Ala
        475                 480                 485

CTG GGG CCA GAT GGT AAG CCC TCC CGT ATC GTA GTT ATC TAC ACG ACG       720
Leu Gly Pro Asp Gly Lys Pro Ser Arg Ile Val Val Ile Tyr Thr Thr
490                 495                 500                 505

GGG AGT CAG GCA ACT ATG GAT GAA CGA AAT AGA CAG ATC GCT GAG ATA       768
Gly Ser Gln Ala Thr Met Asp Glu Arg Asn Arg Gln Ile Ala Glu Ile
                510                 515                 520

GGT GCC TCA CTG ATT AAG CAT TGG                                       792
Gly Ala Ser Leu Ile Lys His Trp
            525

(2) INFORMATION FOR SEQ ID NO:8:

(i) SEQUENCE CHARACTERISTICS:
        (A) LENGTH: 264 amino acids
        (B) TYPE: amino acid
        (D) TOPOLOGY: linear (ii) MOLECULE TYPE: protein (xi) SEQUENCE DESCRIPTION: SEQ ID NO:8:

Met Asp Pro Glu Thr Leu Val Lys Val Lys Asp Ala Glu Asp Gln Leu
  1               5                  10                  15

Gly Ala Arg Val Gly Tyr Ile Glu Leu Asp Leu Asn Ser Gly Lys Ile
                 20                  25                  30

Leu Glu Ser Phe Arg Pro Glu Glu Arg Phe Pro Met Met Ser Thr Phe
             35                  40                  45

Lys Val Leu Leu Cys Gly Ala Val Leu Ser Arg Ile Asp Ala Gly Gln
 50                  55                  60

Glu Gln Leu Gly Arg Arg Ile His Tyr Ser Gln Asn Asp Leu Val Glu
 65                  70                  75                  80

Tyr Ser Pro Val Thr Glu Lys His Leu Thr Asp Gly Met Thr Val Arg
                 85                  90                  95

Glu Leu Cys Ser Ala Ala Ile Thr Met Ser Asp Asn Thr Ala Ala Asn
            100                 105                 110

Leu Leu Leu Thr Thr Ile Gly Gly Pro Lys Glu Leu Thr Ala Phe Leu
            115                 120                 125

His Asn Met Gly Asp His Val Thr Arg Leu Asp His Trp Glu Pro Glu
130                 135                 140

Leu Asn Glu Ala Ile Pro Asn Asp Glu Arg Asp Thr Thr Met Pro Val
145                 150                 155                 160

Ala Met Ala Thr Thr Leu Arg Lys Leu Leu Thr Gly Glu Leu Leu Thr
                165                 170                 175

Leu Ala Ser Arg Gln Gln Leu Ile Asp Trp Met Glu Ala Asp Lys Val
            180                 185                 190

Ala Gly Pro Leu Leu Arg Ser Ala Leu Pro Ala Gly Trp Phe Ile Ala
        195                 200                 205

Asp Lys Ser Gly Ala Gly Glu Arg Gly Ser Arg Gly Ile Ile Ala Ala
```

-continued

```
              210                 215                 220
Leu Gly Pro Asp Gly Lys Pro Ser Arg Ile Val Val Ile Tyr Thr Thr
225                 230                 235                 240

Gly Ser Gln Ala Thr Met Asp Glu Arg Asn Arg Gln Ile Ala Glu Ile
                245                 250                 255

Gly Ala Ser Leu Ile Lys His Trp
                260
```

(2) INFORMATION FOR SEQ ID NO:9:

(i) SEQUENCE CHARACTERISTICS:
        (A) LENGTH: 786 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..786

(xi) SEQUENCE DESCRIPTION: SEQ ID NO:9:

```
ATG AAA GAT GAT TTT GCA AAA CTT GAG GAA CAA TTT GAT GCA AAA CTC       48
Met Lys Asp Asp Phe Ala Lys Leu Glu Glu Gln Phe Asp Ala Lys Leu
265                 270                 275                 280

GGG ATC TTT GCA TTG GAT ACA GGT ACA AAC CGG ACG GTA GCG TAT CGG       96
Gly Ile Phe Ala Leu Asp Thr Gly Thr Asn Arg Thr Val Ala Tyr Arg
                285                 290                 295

CCG GAT GAG CGT TTT GCT TTT GCT TCG ACG ATT AAG GCT TTA ACT GTA      144
Pro Asp Glu Arg Phe Ala Phe Ala Ser Thr Ile Lys Ala Leu Thr Val
                300                 305                 310

GGC GTG CTT TTG CAA CAG AAA TCA ATA GAA GAT CTG AAC CAG AGA ATA      192
Gly Val Leu Leu Gln Gln Lys Ser Ile Glu Asp Leu Asn Gln Arg Ile
                315                 320                 325

ACA TAT ACA CGT GAT GAT CTT GTA AAC TAC AAC CCG ATT ACG GAA AAG      240
Thr Tyr Thr Arg Asp Asp Leu Val Asn Tyr Asn Pro Ile Thr Glu Lys
                330                 335                 340

CAC GTT GAT ACG GGA ATG ACG CTC AAA GAG CTT GCG GAT GCT TCG CTT      288
His Val Asp Thr Gly Met Thr Leu Lys Glu Leu Ala Asp Ala Ser Leu
345                 350                 355                 360

CGA TAT AGT GAC AAT GCG GCA CAG AAT CTC ATT CTT AAA CAA ATT GGC      336
Arg Tyr Ser Asp Asn Ala Ala Gln Asn Leu Ile Leu Lys Gln Ile Gly
                365                 370                 375

GGA CCT GAA AGT TTG AAA AAG GAA CTG AGG AAG ATT GGT GAT GAG GTT      384
Gly Pro Glu Ser Leu Lys Lys Glu Leu Arg Lys Ile Gly Asp Glu Val
                380                 385                 390

ACA AAT CCC GAA CGA TTC GAA CCA GAG TTA AAT GAA GTG AAT CCG GGT      432
Thr Asn Pro Glu Arg Phe Glu Pro Glu Leu Asn Glu Val Asn Pro Gly
                395                 400                 405

GAA ACT CAG GAT ACC AGT ACA GCA AGA GCA CTT GTC ACA AGC CTT CGA      480
Glu Thr Gln Asp Thr Ser Thr Ala Arg Ala Leu Val Thr Ser Leu Arg
410                 415                 420

GCC TTT GCT CTT GAA GAT AAA CTT CCA AGT GAA AAA CGC GAG CTT TTA      528
Ala Phe Ala Leu Glu Asp Lys Leu Pro Ser Glu Lys Arg Glu Leu Leu
425                 430                 435                 440

ATC GAT TGG ATG AAA CGA AAT ACC ACT GGA GAC GCC TTA ATC CGT GCC      576
Ile Asp Trp Met Lys Arg Asn Thr Thr Gly Asp Ala Leu Ile Arg Ala
                445                 450                 455

GGA GCG GCA TCA TAT GGA ACC CGG AAT GAC ATT GCC ATC ATT TGG CCG      624
Gly Ala Ala Ser Tyr Gly Thr Arg Asn Asp Ile Ala Ile Ile Trp Pro
                460                 465                 470

CCA AAA GGA GAT CCT GTC GGT GTG CCG AAC GGT TGG GAA GTG GCT GAT      672
Pro Lys Gly Asp Pro Val Gly Val Pro Asn Gly Trp Glu Val Ala Asp
```

```
                    475                 480                 485
AAA ACT GTT CTT GCA GTA TTA TCC AGC AGG GAT AAA AAG GAC GCC AAG          720
Lys Thr Val Leu Ala Val Leu Ser Ser Arg Asp Lys Lys Asp Ala Lys
    490                 495                 500

TAT GAT GAT AAA CTT ATT GCA GAG GCA ACA AAG GTG GTA ATG AAA GCC          768
Tyr Asp Asp Lys Leu Ile Ala Glu Ala Thr Lys Val Val Met Lys Ala
505                 510                 515                 520

TTA AAC ATG AAC GGC AAA                                                  786
Leu Asn Met Asn Gly Lys
                525
```

(2) INFORMATION FOR SEQ ID NO:10:

(i) SEQUENCE CHARACTERISTICS:
        (A) LENGTH: 262 amino acids
        (B) TYPE: amino acid
        (D) TOPOLOGY: linear (ii) MOLECULE TYPE: protein (xi) SEQUENCE DESCRIPTION: SEQ ID NO:10:

```
Met Lys Asp Asp Phe Ala Lys Leu Glu Glu Gln Phe Asp Ala Lys Leu
1               5                   10                  15

Gly Ile Phe Ala Leu Asp Thr Gly Thr Asn Arg Thr Val Ala Tyr Arg
            20                  25                  30

Pro Asp Glu Arg Phe Ala Phe Ala Ser Thr Ile Lys Ala Leu Thr Val
        35                  40                  45

Gly Val Leu Leu Gln Gln Lys Ser Ile Glu Asp Leu Asn Gln Arg Ile
    50                  55                  60

Thr Tyr Thr Arg Asp Asp Leu Val Asn Tyr Asn Pro Ile Thr Glu Lys
65                  70                  75                  80

His Val Asp Thr Gly Met Thr Leu Lys Glu Leu Ala Asp Ala Ser Leu
                85                  90                  95

Arg Tyr Ser Asp Asn Ala Ala Gln Asn Leu Ile Leu Lys Gln Ile Gly
            100                 105                 110

Gly Pro Glu Ser Leu Lys Lys Glu Leu Arg Lys Ile Gly Asp Glu Val
        115                 120                 125

Thr Asn Pro Glu Arg Phe Glu Pro Glu Leu Asn Glu Val Asn Pro Gly
    130                 135                 140

Glu Thr Gln Asp Thr Ser Thr Ala Arg Ala Leu Val Thr Ser Leu Arg
145                 150                 155                 160

Ala Phe Ala Leu Glu Asp Lys Leu Pro Ser Glu Lys Arg Glu Leu Leu
                165                 170                 175

Ile Asp Trp Met Lys Arg Asn Thr Thr Gly Asp Ala Leu Ile Arg Ala
            180                 185                 190

Gly Ala Ala Ser Tyr Gly Thr Arg Asn Asp Ile Ala Ile Ile Trp Pro
        195                 200                 205

Pro Lys Gly Asp Pro Val Gly Val Pro Asp Gly Trp Glu Val Ala Asp
    210                 215                 220

Lys Thr Val Leu Ala Val Leu Ser Ser Arg Asp Lys Lys Asp Ala Lys
225                 230                 235                 240

Tyr Asp Asp Lys Leu Ile Ala Glu Ala Thr Lys Val Val Met Lys Ala
                245                 250                 255

Leu Asn Met Asn Gly Lys
            260
```

METHODS AND COMPOSITIONS FOR SENSITIVE AND RAPID, FUNCTIONAL IDENTIFICATION OF GENOMIC POLYNUCLEOTIDES AND SECONDARY SCREENING CAPABILITIES

TECHNICAL FIELD

The present invention generally relates to methods and compositions for the identification of useful and functional portions of the genome and compounds for modulating such portions of the genome, particularly the identification of proteins that are directly or indirectly transcriptionally regulated and compounds for regulating such proteins, either directly or indirectly.

BACKGROUND

The identification and isolation of useful portions of the genome requires extensive expenditure of time and financial resources. Currently, many genome projects sequence genes use various strategies to reduce cloning and sequencing times. While genome projects rapidly expand the database of genetic material, such projects often lack the ability to integrate the information with the biology of the cell or organism from which the genes were isolated. In some instances, coding regions of newly isolated genes reveal sequence homology to other genes of known function. This type of analysis can, at best, provide clues as to the possible relationships between different genes and proteins. Genomic projects in general, however, suffer from the inability to rapidly and directly isolate and identify specific, yet unknown, genes associated with particular a biological process or processes.

The evaluation of the function of genes identified from genomic sequencing projects requires cloning the discovered gene into an expression system suitable for functional screening. Transferring the discovered gene into a functional screening system requires additional expenditure of time and resources without a guarantee that the correct screening system was chosen. Since the function of the discovered gene is unknown or only surmised by inference to related genes, the chosen screening system may not have any relationship to the biological function of the gene. Further, if negative results are obtained in the screen, it can not be easily determined whether 1) the gene or gene product is not functioning properly in the screening assay or 2) the gene or gene product is directly or indirectly involved in the biological process being assayed by the screening system.

Consequently, there is a need to provide methods and compositions for rapidly isolating portions of genomes associated with a known biological process and to screen such portions of genomes for activity without the necessity of transferring the gene of interest into an additional screening system.

SUMMARY

Figure 1:
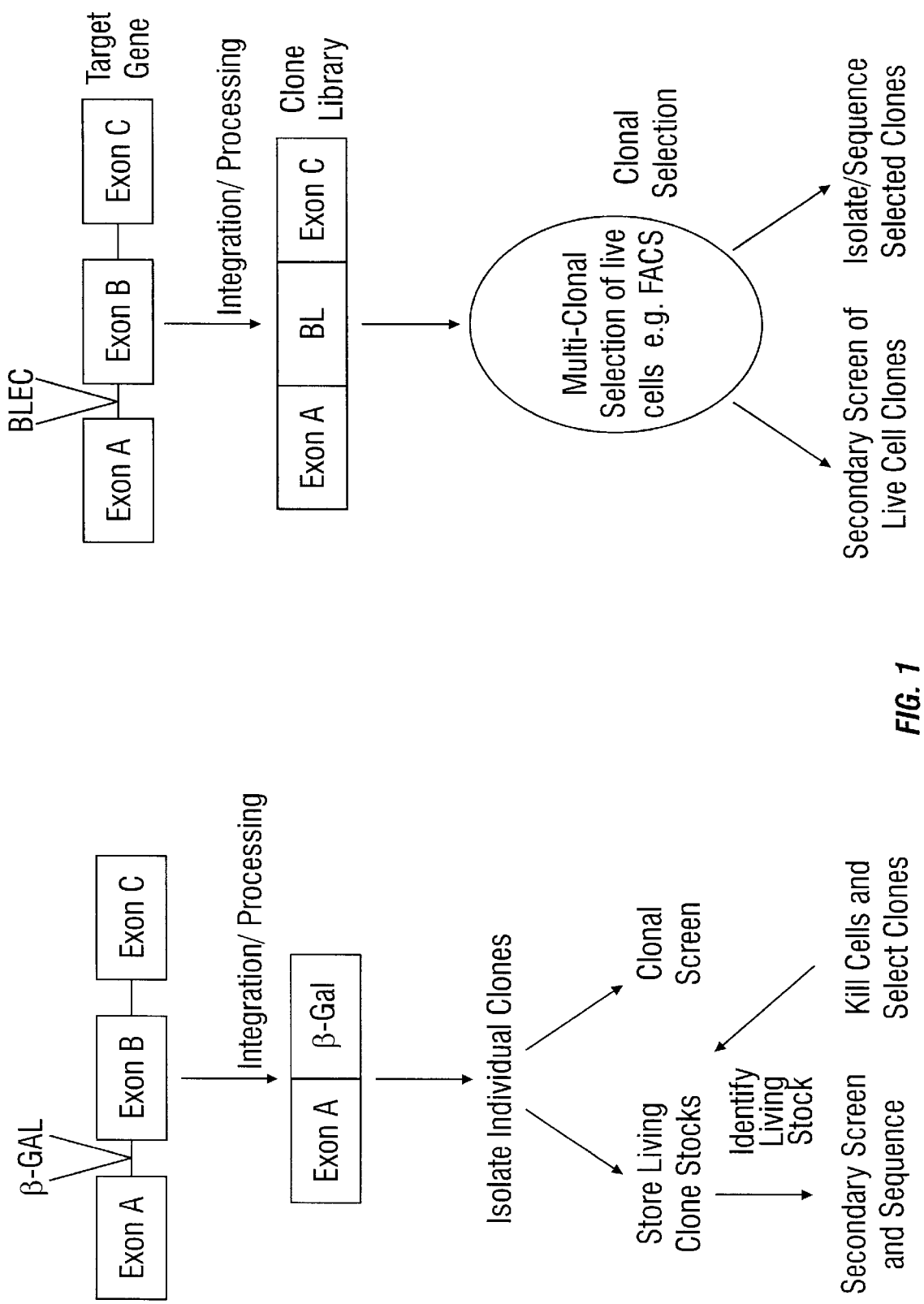
FIG. 1 shows a comparison between the prior art and one embodiment of the invention. The prior art uses the b-gal reporter and requires the establishment of clones prior to expression analysis. One embodiment of this invention allows for the rapid identification of living cell clones from large multiclonal populations of BLEC (beta-lactamase expression construct) integrated cells. This is a significant advancement over the prior art, which requires the analysis of individual clones followed by the retrieving of selected clone from a duplicate clonal stock of living cells.

The present invention recognizes that BL (beta-lactamase) polynucleotides can be effectively used in living eukaryotic cells to functionally identify active portions of a genome directly or indirectly associated with a biological process. The present invention also recognizes for the first time that BL activity can be measured using membrane permeant substrates in living cells incubated with a test compound that directly or indirectly interacts with a portion of the genome having an integrated BL polynucleotide. The present invention, thus, permits the rapid identification and isolation of genomic polynucleotides indirectly or directly associated with a defined biological process and identification of compounds that modulate such processes and regions of the genome. Because the identification of active genomic polynucleotides is permitted in living cells, further functional characterization can be conducted using the same cells, and optionally, the same screening assay. The ability to functionally screen immediately after the rapid identification of a functionally active portion of a genome, without the necessity of transferring the identified portion of the genome into a secondary screening system, represents, among other things, a distinct advantage over the prior art, as shown in FIG. 1.

The invention provides for a method of identifying portions of a genome, e.g. genomic polynucleotides, in a living cell using a polynucleotide encoding a protein with BL activity that can be detected with a membrane permeant BL substrate. Typically, the method involves inserting a polynucleotide encoding a protein with BL activity into the genome of an organism using any method known in the art, developed in the future or described herein. Usually, a BL expression construct will be used into integrate a BL polynucleotide into a eukaryotic genome, as described herein. The cell, such as a eukaryotic cell, is usually contacted with a predetermined concentration of a modulator, either before or after integration of the BL polynucleotide. BL activity is usually then measured inside the living cell, preferably with fluorescent, membrane permeant BL substrates that are transformed by the cell into membrane impermeant BL substrates as described herein.

The invention also provides for a method of identifying proteins or compounds that directly or indirectly modulate a genomic polynucleotide. Generally, the method comprises inserting a BL expression construct into an eukaryotic genome, usually non-yeast, contained in at least one living cell, contacting the cell with a predetermined concentration of a modulator, and detecting BL activity in the cell.

The invention also provides for a method of screening compounds with an active genomic polynucleotide that comprises: 1) optionally contacting a multiclonal population of cells with a first test compound prior to separating said cells by a FACS, 2) separating by a FACS said multiclonal population of cells into BL expressing cells and non-BL expressing cells, wherein said BL expressing cells have a detectable difference in cellular fluorescence properties compared to non-BL expressing cells, 3) contacting either population of cells with the same or a different test compound, and 4) optionally repeating step (2), wherein said multiclonal population of cells comprises eukaryotic cells having a BL expression construct integrated into a genome of said eukaryotic cells and a membrane permanent BL substrate transformed inside said cells to a membrane impermeant BL substrate. The steps of this method can be repeated to permit additional characterization of identified clones.

DETAILED DESCRIPTION OF THE INVENTION

Definitions

Unless defined otherwise, all technical and scientific terms used herein have the same meaning as commonly understood by one of ordinary skill in the art to which this invention belongs. Generally, the nomenclature used herein and the laboratory procedures in cell culture, molecular genetics, and nucleic acid chemistry and hybridization described below are those well known and commonly employed in the art. Standard techniques are used for recombinant nucleic acid methods, polynucleotide synthesis, and microbial culture and transformation (e.g., electroporation, lipofection). Generally, enzymatic reactions and purification steps are performed according to the manufacturer's specifications. The techniques and procedures are generally performed according to conventional methods in the art and various general references (see generally, Sambrook et al. Molecular Cloning: A Laboratory Manual, 2d ed. (1989) Cold Spring Harbor Laboratory Press, Cold Spring Harbor, N.Y., which is incorporated herein by reference) which are provided throughout this document. The nomenclature used herein and the laboratory procedures in analytical chemistry, organic synthetic chemistry, and pharmaceutical formulation described below are those well known and commonly employed in the art. Standard techniques are used for chemical syntheses, chemical analyses, pharmaceutical formulation and delivery, and treatment of patients. As employed throughout the disclosure, the following terms, unless otherwise indicated, shall be understood to have the following meanings:

"Fluorescent donor moiety" refers to the radical of a fluorogenic compound which can absorb energy and is capable of transferring the energy to another fluorogenic molecule or part of a compound. Suitable donor fluorogenic molecules include, but are not limited to, coumarins and related dyes xanthene dyes such as fluoresceins, rhodols, and rhodamines, resorufins, cyanine dyes, bimanes, acridines, isoindoles, dansyl dyes, aminophthalic hydrazides such as luminol and isoluminol derivatives, aminophthalimides, aminonaphthalimides, aminobenzofurans, aminoquinolines, dicyanohydroquinones, and europium and terbium complexes and related compounds.

"Quencher" refers to a chromophoric molecule or part of a compound which is capable of reducing the emission from a fluorescent donor when attached to the donor. Quenching may occur by any of several mechanisms including fluorescence resonance energy transfer, photoinduced electron transfer, paramagnetic enhancement of intersystem crossing, Dexter exchange coupling, and exciton coupling such as the formation of dark complexes.

"Acceptor" refers to a quencher which operates via fluorescence resonance energy transfer. Many acceptors can re-emit the transferred senergy as fluorescence. Examples include coumarins and related fluorophores, xanthenes such as fluoresceins, rhodols, and rhodamines, resorufins, cyanines, difluoroboradiazaindacenes, and phthalocyanines. Other chemical classes of acceptors generally do not re-emit the transferred energy. Examples include indigos, benzoquinones, anthraquinones, azo compounds, nitro compounds, indoanilines, di- and triphenylmethanes.

"Dye" refers to a molecule or part of a compound which absorbs specific frequencies of light, including but not limited to ultraviolet light. The terms "dye" and "chromophore" are synonymous.

"Fluorophore" refers to a chromophore which fluoresces.

"Membrane-permeant derivative" refers a chemical derivative of a compound of general formula II wherein at least one of X and Y contains at least one acylated aromatic hydroxyl, acylated amine, or alkylated aromatic hydroxyl wherein the acyl group contains 1 to 5 carbon atoms and wherein the alkyl group is selected from the group consisting of —$CH_2OC(O)$alk, —$CH_2SC(O)$alk, —$CH_2OC(O)$Oalk, lower acyloxy-alpha-benzyl, and deltabutyrolactonyl; wherein alk is lower alkyl of 1 to 4 carbon atoms. These derivatives are made better able to cross cell membranes, i.e. membrane permeant, because hydrophilic groups are masked to provide more hydrophobic derivatives. Also, the masking groups are designed to be cleaved from the fluorogenic substrate within the cell to generate the derived substrate intracellularly. Because the substrate is more hydrophilic than the membrane permeant derivative it is now trapped within the cells.

"Alkyl" refers to straight, branched, and cyclic aliphatic groups of 1 to 8 carbon atoms, preferably 1 to 6 carbon atoms, and most preferably 1 to 4 carbon atoms. The term "lower alkyl" refers to straight and branched chain alkyl groups of 1 to 4 carbon atoms.

"Aliphatic" refers to saturated and unsaturated alkyl groups of 1 to 10 carbon atoms, preferably 1 to 6 carbon atoms, and most preferably 1 to 4 carbon atoms.

"Isolated polynucleotide" refers a polynucleotide of genomic, cDNA, or synthetic origin or some combination there of, which by virtue of its origin the "isolated polynucleotide" (1) is not associated with the cell in which the "isolated polynucleotide" is found in nature, or (2) is operably linked to a polynucleotide which it is not linked to in nature.

"Isolated protein" refers a protein of cDNA, recombinant RNA, or synthetic origin or some combination thereof, which by virtue of its origin the "isolated protein" (1) is not associated with proteins found it is normally found with in nature, or (2) is isolated from the cell in which it normally occurs or (3) is isolated free of other proteins from the same cellular source, e.g. free of human proteins, or (4) is expressed by a cell from a different species, or (5) does not occur in nature.

"Polypeptide" as used herein as a generic term to refer to native protein, fragments, or analogs of a polypeptide sequence. Hence, native protein, fragments, and analogs are species of the polypeptide genus. Preferred, BL polypeptides include those with the polypeptide sequence represented in the SEQUENCE ID. LISTING and any other polypeptide or protein having similar BL activity as measured by one or more of the assays described herein. BL polypeptide or proteins can include any protein having sufficient activity for detection in the assays described herein.

"Naturally-occurring" as used herein, as applied to an object, refers to the fact that an object can be found in nature. For example, a polypeptide or polynucleotide sequence that is present in an organism (including viruses) that can be isolated from a source in nature and which has not been intentionally modified by man in the laboratory is naturally-occurring.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

"Control sequence" refers to polynucleotide sequences which are necessary to effect the expression of coding and non-coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, components whose presence can influence expression, and can also include additional components whose presence is advantageous, for example, leader sequences and fusion partner sequences.

"Polynucleotide" refers to a polymeric form of nucleotides of at least 10 bases in length, either ribonucleotides or deoxynucleotides or a modified form of either type of nucleotide. The term includes single and double stranded forms of DNA. "Genomic polynucleotide" refers to a portion of a genome. "Active genomic polynucleotide" or "active portion of a genome" refer to regions of a genome that can be up-regulated, down-regulated or both, either directly or indirectly, by a biological process. "Directly," in the context of a biological process or processes, refers to direct causation of a process that does not require intermediate steps, usually caused by one molecule contacting or binding to another molecule (the same type or different type of molecule). For example, molecule A contacts molecule B, which causes molecule B to exert effect X that is part of a biological process. "Indirectly," in the context of a biological process or processes, refers to indirect causation that requires intermediate steps, usually caused by two or more direct steps. For example, molecule A contacts molecule B to exert effect X which in turn causes effect Y.

"BL" refers to beta-lactamase.

"BL polynucleotide" refers to a polynucleotide encoding a protein with BL activity. Preferably, the protein with BL activity can measured be in a FACS at 22 degrees using a CCF2-AM BL substrate at a level of about 1,000 such protein molecules or less per cell. More preferably, the protein with BL activity can measured be in a FACS at 22 degrees using a CCF2-AM BL substrate at a level of about 300 to 1,000 such protein molecules per cell. More preferably, the protein with BL activity can measured be in a FACS at 22 degrees using a CCF2-AM BL substrate at a level of about 25 to 300 such protein molecules per cell. Proteins with BL activity that require more than 1,000 molecules of such protein per cell for detection with a FACS at 22 degrees using a CCF2-AM BL substrate can be used and preferably have at least 5% of the activity of the protein with SEQ. ID. NO.:1.

"Sequence homology" refers to the proportion of base matches between two nucleic acid sequences or the proportion amino acid matches between two amino acid sequences. When sequence homology is expressed as a percentage, e.g., 50%, the percentage denotes the proportion of matches over the length of sequence from a desired sequence (e.g. BL sequences, such as SEQ. ID. NO.:1) that is compared to some other sequence. Gaps (in either of the two sequences) are permitted to maximize matching; gap lengths of 15 bases or less are usually used, 6 bases or less are preferred with 2 bases or less more preferred. When using oligonucleotides as probes or treatments the sequence homology between the target nucleic acid and the oligonucleotide sequence is generally not less than 17 target base matches out of 20 possible oligonucleotide base pair matches (85%); preferably not less than 9 matches out of 10 possible base pair matches (90%), and most preferably not less than 19 matches out of 20 possible base pair matches (95%).

"Selectively hybridize" refers to detectably and specifically bind. Polynucleotides, oligonucleotides and fragments of the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments related to the invention and a nucleic acid sequence of interest will be at least 30%, and more typically with preferably increasing homologies of at least 40%, 50%, 60%, 70%, and 90%.

Typically, hybridization and washing conditions are performed at high stringency according to conventional hybridization procedures. Positive clones are isolated and sequenced. For illustration and not for limitation, a full-length polynucleotide corresponding to the nucleic acid sequence of SEQ. ID.NO.:1 may be labeled and used as a hybridization probe to isolate genomic clones from a human genomic clone library in λEMBL4 or λGEM11 (Promega Corporation, Madison, Wis.); typical hybridization conditions for screening plaque lifts (Benton and Davis (1978) Science 196: 180) can be: 50% formamide, 5×SSC or SSPE, 1–5× Denhardt's solution, 0.1–1% SDS, 100–200 $\mu$g sheared heterologous DNA or tRNA, 0–10% dextran sulfate, $1\times10^5$ to $1\times10^7$ cpm/ml of denatured probe with a specific activity of about $1\times10^8$ cpm/$\mu$g, and incubation at 42° C. for about 6–36 hours. Prehybridization conditions are essentially identical except that probe is not included and incubation time is typically reduced. Washing conditions are typically 1–3×SSC, 0.1–1% SDS, 50–70° C. with change of wash solution at about 5–30 minutes. Cognate sequences, including allelic sequences, can be obtained in this manner.

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, 1972, volume 5, National Biomedical Research Foundation, pp. 101–110, and Supplement 2 to this volume, pp.1–10. The two sequences or parts thereof are more preferably homologous if their amino acids are greater than or equal to 30% identical when optimally aligned using the ALIGN program.

"Corresponds to" refers to a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing such as a SEQ. ID. NO.: 1, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 30 percent sequence identity, preferably at least 50 to 60 percent sequence identity, more usually at least 60 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison.

As applied to polypeptides, the term "substantial identity" means that two peptide sequences, when optimally aligned, such as by the programs GAP or BESTFIT using default gap weights, share at least 30 percent sequence identity, preferably at least 40 percent sequence identity, more preferably at least 50 percent sequence identity, and most preferably at least 60 percent sequence identity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

"Polypeptide fragment" refers to a polypeptide that has an amino-terminal and/or carboxy-terminal deletion, but where the remaining amino acid sequence is usually identical to the corresponding positions in the naturally-occurring sequence deduced, for example, from a full-length cDNA sequence (e.g., the sequence shown in SEQ. ID. NO.:1). Fragments typically are at least 5, 6, 8 or 10 amino acids long, preferably at least 14 amino acids long, more preferably at least 20 amino acids long, usually at least 50 amino acids long, and even more preferably at least 70 amino acids long.

"BL polypeptides fragment" refers to polypeptides which are comprised of a segment of at least 25 amino acids that has substantial identity to a portion of the deduced amino acid sequence shown in SEQ. ID. NO.:1 and which has at least one of the following properties: (1) specific binding to a BL substrate, preferably cephalosporin, under suitable binding conditions, or (2) the ability to effectuate enzymatic activity, preferably cephalosporin backbone cleavage activity, when expressed in a mammalian cell. Typically, analog polypeptides comprise a conservative amino acid substitution (or addition or deletion) with respect to the naturally-occurring sequence. Analogs typically are at least 20 amino acids long, preferably at least 50 amino acids long or longer, most usually being as long as full-length naturally-occurring polypeptide.

"Modulation" refers to the capacity to either enhance or inhibit a functional property of biological activity or process (e.g., enzyme activity or receptor binding); such enhancement or inhibition may be contingent on the occurrence of a specific event, such as activation of a signal transduction pathway, and/or may be manifest only in particular cell types.

The term "modulator" refers to a chemical compound (naturally occurring or non-naturally occurring), such as a biological macromolecule (e.g. nucleic acid, protein, non-peptide, or organic molecule), or an extract made from biological materials such as bacteria, plants, fungi, or animal (particularly mammalian) cells or tissues. Modulators are evaluated for potential activity as inhibitors or activators (directly or indirectly) of a biological process or processes (e.g., agonist, partial antagonist, partial agonist, antagonist, antineoplastic agents, cytotoxic agents, inhibitors of neoplastic transformation or cell proliferation, cell proliferation-promoting agents, and the like) by inclusion in screening assays described herein. The activity of a modulator may be known, unknown or partial known.

The term "test compound" refers to a compound to be tested by one or more screening method(s) of the invention as a putative modulator.

The terms "label" or "labeled" refers to incorporation of a detectable marker, e.g., by incorporation of a radiolabeled amino acid or attachment to a polypeptide of biotinyl moieties that can be detected by marked avidin (e.g., strepta-vidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes (e.g., $^3$H, $^{14}$C, $^{35}$S, $^{125}$I, 131I), fluorescent labels (e.g., FITC, rhodamine, lanthanide phosphors), enzymatic labels (or reporter genes) (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

"Substantially pure" refers to an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

"Pharmaceutical agent or drug" refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference).

Introduction

The present invention recognizes that BL polynucleotides can be effectively used in living eukaryotic cells to functionally identify active portions of a genome directly or indirectly associated with a biological process. The present invention also recognizes for the first time that BL activity can be measured using membrane permeant substrates in living cells incubated with a test compound that directly or indirectly interacts with a portion of the genome having an integrated BL polynucleotide. The present invention, thus, permits the rapid identification and isolation of genomic polynucleotides indirectly or directly associated with a defined biological process and identification of compounds that modulate such processes and regions of the genome. Because the identification of active genomic polynucleotides is permitted in living cells, further functional characterization can be conducted using the same cells, and optionally, the same screening assay. The ability to functionally screen immediately after the rapid identification of a functionally active portion of a genome, without the necessity of transferring the identified portion of the genome into a secondary screening system, represents, among other things, a distinct advantage over the prior art, as shown in FIG. 1.

As a non-limiting introduction to the breadth of the invention, the invention includes several general and useful aspects, including:

1) a method for identifying genes or gene products directly or indirectly associated (e.g. regulated) with a biological process of interest (that can be modulated by a compound) using a genomic polynucleotide operably linked to a polynucleotide encoding a protein with BL activity, 2) a method for identifying proteins (e.g. orphan proteins or known proteins) or compounds that directly or indirectly modulate (e.g. activate or inhibit transcription) a genomic polynucleotide operably linked to a polynucleotide encoding a protein with BL activity, 3) a method of screening for an active genomic polynucleotide (e.g. enhancer, promoter or coding region in the genome) that can be directly or indirectly associated (e.g. regulated) with a biological process of interest (that can be modulated by a compound) using a genomic polynucleotide operably linked to a polynucleotide encoding a protein with BL activity that can be detected by FACS using a fluorescent, membrane permeant BL substrate, 4) eukaryotic cells with a genomic polynucleotide operably linked to a polynucleotide encoding a protein with BL activity, and 5) polynucleotides related to the above methods and cells.

These aspects of the invention, as well as others described herein, can be achieved by using the methods and compositions of matter described herein. To gain a full appreciation of the scope of the invention, it will be further recognized that various aspects of the invention can be combined to make desirable embodiments of the invention. For example, the invention includes a method of identifying compounds that modulate active genomic polynucleotides operably linked to a protein with BL activity that can be detected by FACS using a fluorescent, membrane permeant BL substrate. Such combinations result in particularly useful and robust embodiments of the invention.

Methods for Rapidly Identifying Functional Portions of a Genome

The invention provides for a method of identifying portions of a genome, e.g. genomic polynucleotides, in a living cell using a polynucleotide encoding a protein with BL activity that can be detected with a membrane permeant BL substrate. Typically, the method involves inserting a polynucleotide encoding a protein with BL activity into the genome of an organism using any method known in the art, developed in the future or described herein. Usually, a BL expression construct will be used into integrate a BL polynucleotide into a eukaryotic genome, as described herein.

The cell, such as a eukaryotic cell, is usually contacted with a predetermined concentration of a modulator, either before or after integration of the BL polynucleotide. BL activity is usually then measured inside the living cell, preferably with fluorescent, membrane permeant BL substrates that are transformed by the cell into membrane impermeant BL substrates as described herein.

Once BL polynucleotides are integrated into the genome of interest, they become under the transcriptional control of the genome of the host cell. Integration into the genome is usually stable, as described herein and known in the art. Transcriptional control of the genome often results from receptor activation, which can regulate transcriptional and translational events to change the amount of protein present in the cell. The amount of protein present with BL activity can be measured via its enzymatic action on a substrate. Normally, the substrate is a small uncharged molecule that, when added to the extracellular solution, can penetrate the plasma membrane to encounter the enzyme. A charged molecule can also be employed, but the charges need to be masked by groups that will be cleaved by endogenous or heterologous cellular enzymes or processes (e.g., esters cleaved by cytoplasmic esterases). As described more fully herein and in U.S. patent application Ser. No. 08/407,544, filed Mar. 20, 1995 by Tsien et al and PCT application/ US96/04059, filed Mar. 20, 1996 by Tsien et al (both of which are herein incorporated by reference), the use of substrates which exhibit changes in their fluorescence spectra upon interaction with an enzyme are particularly desirable. In some assays, the fluorogenic substrate is converted to a fluorescent product by BL activity. Alternatively, the fluorescent substrate changes fluorescence properties upon conversion by BL activity. Preferably, the product should be very fluorescent to obtain a maximal signal, and very polar, to stay trapped inside the cell.

BL polynucleotides can be placed on a variety of plasmids for integration into a genome and to identify genes from a large variety of organisms [Gorman, C. M. et al., Mol. Cell Biol. 2: 1044–1051 (1982); Alam, J. and Cook, J. L., Anal. Biochem. 188: 245–254, (1990)]. Standard techniques are used to introduce these polynucleotides into a cell or whole organism [e.g., as described in Sambrook, J., Fritsch, E. F. and Maniatis, T. Expression of cloned genes in cultured mammalian cells. In: Molecular Cloning, edited by Nolan, C. N.Y.: Cold Spring Harbor Laboratory Press, 1989]. Resistance markers can be used to select for successfully transfected cells.

If a BL expression construct is selected for integrating a BL polynucleotide into a eukaryotic genome, it will usually contain at least a BL polynucleotide operably linked to a splice acceptor and optionally a splice donor. Alternatively, the BL polynucleotide may be operably linked to any means for integrating a polynucleotide into a genome, preferably for integration into the coding region of a gene within the genome and in frame. The BL expression construct can optionally comprise, depending on the application, an IRES element, a splice donor, a poly A site, translational start site (e.g. a Kozak sequence) and a selectable marker.

Preferably, BL polynucleotides encode a cytosolic form of a protein with BL activity. This provides the advantage of trapping the normally secreted BL protein within the cell, which enhances signal to noise ratio of the signal associated with BL activity. Usually, this is accomplished by removing or disabling the signal sequence normally present for secretion. As used herein, "cytosolic protein with BL activity" refers to a protein with β-lactamase activity that lacks the proper amino acid sequences for secretion from the cell, e.g., the signal sequence. For example, in the polypeptide of SEQ. ID NO.: 1, the signal sequence has been replaced with the amino acids Met-Ser. Accordingly, upon expression, β-lactamase activity remains within the cell. For expression in mammalian cells it is preferably to use BL Polynucleotides with nucleotide sequences preferred by mammalian cells.

Proteins with β-lactamase activity can be any known to the art, developed in the future or described herein. This includes, for example, the enzymes represent by SEQ. ID. NO.'s described herein. Nucleic acids encoding proteins with β-lactamase activity can be obtained by methods known in the art, for example, by polymerase chain reaction of cDNA using primers based on the DNA sequence in SEQ. ID. NO.: 1. PCR methods are described in, for example, U.S. Pat. No. 4,683,195; Mullis et al. (1987) *Cold Spring Harbor Symp. Quant. Biol.* 51:263; and Erlich, ed., *PCR Technology*, (Stockton Press, N.Y., 1989).

The splice site acceptor is operably linked to the BL polynucleotide to facilitate expression upon integration into an intron. Usually, a fusion RNA will be created with the coding region of an adjacent operably portion of the exon. A splice acceptor sequence is a sequence at the 3' end of an intron where it junctions with an exon. The consensus sequences for a splice acceptor is NTN(TC) (TC) (TC)TTT (TC) (TC)(TC) (TC) (TC) (TC)NCAGg. The intronic sequences are represented by upper case and the exonic sequence by lower case font. These sequences represent those of which are conserved from viral to primate genomes.

The splice site donor is operably linked to the BL polynucleotide to facilitate integration in an intron to promote expression by requiring a poly-adenylation sequence. Usually, a fusion RNA is created with the coding region on the 3' end of the BL polynucleotide. This is preferred when it is desired to sequence the coding region of the identified gene. A splice donor is a sequence is a sequence at the 5' end of an intron where it junctions with an exon. The consensus sequence for a splice donor sequence is naggt(ag)aGT. The intronic sequences are represented by upper case and the exonic sequence by lower case font. Theses sequences represent those of which are conserved from viral to primate genomes.

As an alternative to a splice site donor, a poly A site may operably linked to the BL polynucleotide. A polyadenylation signals, i.e poly A sites, include SV40 poly A sites, such as those described in the Invitrogen Catalog 1996.

In some instances, it may be desirable to include in the BL expression construct that includes a translational start site. For instance, a translational start site allows for BL expression even if the integration occurs in non-coding regions. Usually, such sequences will not reduce the expression of a highly expressed gene. Translational start sites include a "Kozak sequence" and are the preferred sequences for expression in mammalian cells described in Kozak, M., *J. Cell Biol.* 108: 229–241 (1989). The nucleotide sequence for a cytosolic protein with β-lactamase activity in SEQ. ID. NO.: 3 contains a Kozak sequences for the nucleotides-9 to 4 (GGTACCACCATGA).

It is also preferable, when using mammalian cells, to include an IRES (internal ribosome binding site) element in the BL expression construct. Typically, an IRES element will improve the yield of expressing clones. One caveat of integration vectors is that only one in three insertions into an intron will be in frame and produce a functional reporter protein. This limitation can be reduced by cloning an internal-ribosomal-entry-site (IRES) sequence between the splice acceptor site and the reporter gene. This eliminates reading frame restrictions and possible functional inactivation of the reporter protein by fusion to an endogenous protein. IRES elements include those from include piconaviruses, picorna-related viruses, and hepatitis A and C. Preferably, the IRES element is from a polio virus. Specific IRES elements can be found, for instance, in WO9611211 (by Das and Coward published Apr. 16, 1996), EP 585983 (by Zurr published Mar. 7, 1996), WO9601324 (by Berlioz published Jan. 18, 1996) and WO9424301 (by Smith published Oct. 27, 1994), all of which are herein incorporated by reference.

To improve selection of BL polynucleotide into a genome, a selectable marker can be used in the BL expression construct. Selectable markers for mammalian cells are known in the art, and include for example, thymidine kinase, dihydrofolate reductase (together with methotrexate as a DHFR amplifier), aminoglycoside phosphotransferase, hygromycin B phosphotransferase, asparagine synthetase, adenosine deaminase, metallothionien, and antibiotic resistant genes such as genes neomycin resistance. Selectable markers for non-mammalian cells are known in the art and include gene providing resistance to antibiotics, such as kanamycin, tetracycline, and ampicillin.

The invention can be readily practiced with genomes having intron/exon structures. Such genomes include those of mammals (e.g. human, rabbit, mouse, rat, monkey, pig and cow), vertebrates, insects and yeast. Intron-targeted vectors are more commonly used in mammalian cells as introns, or intervening sequences, are considerably larger than exons, or mRNA coding regions in mammals. Intron targeting can be achieved by cloning a splice acceptor or 3' intronic sequences upstream of a BL polynucleotide gene followed by a polyadenylation signal or 5' intronic splice donor site. When the vector inserts into an intron, the reporter gene is expressed under the same control as the gene into which it has inserted.

The invention can also be practiced with genomes having reduced numbers of or lacking intron/exon structures. For lower eukaryotes which have simple genomic organization, i.e. containing few and small introns, exon-targeted vectors can be used. Such vectors include BL polynucleotides operably linked to a poly-adenylation sequence and optionally to an IRES element. Lower eukaryotes include yeast, and fungi and pathogenic eurokaryotes (e.g. parasites and microoganisms). For genomes lacking intron/exon structures restriction enzyme integration, transposon induced integration or selection integration can be used for genomic integration. Such methods include those described by Kuspa and Loomis, PNAS 89: 8803–8807 (1992) and Derbyshire, K. M., Gene Nov. 7: 143–144 (1995). Prokaryotes can be used with the invention if integration can occur in such genomes. Retroviral vectors can also be used to integrate BL polynucleotides into a genome, such as those methods and composition described in U.S. Pat. No. 5,364,783.

Typically, integration will occur in the regions of the genome that are accessible to the integration vector. Such regions are usually active portions of the genome where there is increased genome regulatory activity, e.g. increased polymerase activity or a change in DNA binding by proteins that regulate transcription of the genome. Many embodiments of the invention described herein can result in random integration.

Integration, however, can be directed to regions of the genome active during specific type of genome activity. For instance, integration at sites in the genome that are active during specific phases of the cell cycle can be promoted by synchronizing the cells in a desired phase of the cell cycle. Such cell cycle methods include those known in the art, such as serum deprivation or alpha factors (for yeast). Integration may also be directed to regions of the genome active during cell regulation by a compound, such as an antagonist or agonist for a receptor or some other compound that increase or decreases or other wise modulates genome activity. By adding the compound of interest, genome activity can be increased, often in specific regions to promote integration of an integration vector, including those of the invention, into such regions of the genome. For instance, a nuclear receptor activator (general or specific) could applied to activate the cells prior or during integration in order to promote integration at sites in the genome that become more active during nuclear receptor activation. Such cells could then be screened with the same or different nuclear receptor to identify which clones, and which portions of the genome are active during nuclear receptor activation. Any agonists, antagonists and modulators of the receptors described herein can be used in such a manner, as well as any other compounds that increase or decrease genome activity.

The cells used in the invention will typically correspond to the genome of interest. For example, if regions of the human genome are desired to be identified, then human cells containing a proper genetic complement will generally be used. Libraries, however, could be biased by using cells that contain extra-copies of certain chromosomes or other portions of the genome. Cells that do not correspond to the genome of interest can also be used if the genome of interest or significant portions of the genome of interest can be replicated in the cells.

Additionally, by the appropriate choice of cells and expressed proteins, identification and screening assays can be constructed that detect active portions of the genome associated with a biological process that requires, in whole or part, the presence of a particular protein (protein of interest). Cells can be selected depending on the type of proteins that are expressed (homologously or heterologously) or from the type of tissue from which the cell line or explant was originally generated. If the identification of portions of the genome activated by a particular type of protein is desired, then the cell used should express that protein.

The cells can express the protein homologously, i.e. expression of the desired protein normally or naturally occurs in the cells. Alternatively, the cells can be directed to express a protein heterologously, i.e. expression of the desired protein which does not normally or naturally occur in the cells. Such heterologous expression can be directed by "turning on" the gene in the cell encoding the desired protein or by transfecting the cell with a polynucleotide encoding the desired protein (either by constitutive expression or inducible expression). Inducible expression is preferred if it is thought that the expressed protein of interest may be toxic to the cells.

Such proteins of interest that can be expressed in the cells of the invention include, without limitation: hormone receptors (e.g. mineralcorticosteroid, gluococorticoid, and thyroid hormone receptors); intracellular receptors (e.g. retinoids, vitamin D3 and vitamin A receptors); signaling molecules (e.g kinases, transcription factors, or molecules such signal transducers and activators of transcription) [*Science* Vol. 264, 1994, p.1415–1421; *Mol. Cell Biol.*, Vol. 16, 1996, p.369–375]; receptors of the cytokine superfamily (e.g. erthyropoietin, growth hormone, interferons, and interleukins (other than IL-8) and colony-stimulating factors); G-protein coupled receptors [U.S. Pat. No. 5,436,128]for hormones (e.g. calcitonin, epinephrine or gastrin, pancrine or autocrine mediators, such as stomatostatin or prostaglandins) and neurotransmitters (norepinephrine, dopamine, serotonin or acetylcholine); tyrosine kinase receptors such as insulin growth factor, nerve growth factor [U.S. Pat. No. 5,436,128]. Examples of use of such proteins is further described herein.

Cells comprising BL polynucleotides integrated in the genome can be contacted with test compounds or modulators of a biological process and screened for activity. Usually, the compound being screened will have at least one defined target, usually a protein. The compound is normally applied to the cells to achieve a final predetermined concentration in the medium bathing the cells. Typically, screens are conducted at concentrations 100 uM or less, preferably 10 uM or less and more preferably 1 uM or less. As described more fully herein, cells can be subjected to multiple rounds of screening and selection using the same compound in each round to insure the identification of clones with the desired response to a compound or with different compounds to characterize which compounds produce a response (either an increase or decrease BL activity) in the cells. Such methods can be applied to any compound that alters the function of any the proteins mentioned herein or known in the art.

Compounds, without a defined target, however, can also be used with the cells of the invention. For example, once a clone is identified as containing an active genomic polynucleotide that is activated, for instance by a neurotransmitter, that same clone can be screened by compounds lacking a defined target to determine if activation by the neurotransmitter is blocked or enhanced by the compound. This is a particularly useful method for finding therapeutic targets downstream of receptor activation (in this case a neurotransmitter). Such methods can be applied to any compound that alters the function of any the proteins mentioned herein or known in the art.

The methods and compositions described herein offer a number of advantages over the prior art. For instance, screening of mammalian based gene integration libraries is limited by the use of existing reporter systems. Many enzymatic reporter genes, such as secreted-alkaline phosphatase, and luciferase, cannot be used to assay single living cells (including FACS) because the assay requires cell lysis to determine reporter gene activity. Alternatively, β-galactosidase can detect expression in single cells but substrate loading requires permeabilization of cells, which can cause deleterious effects on normal cell functions. Additionally, the properties of fluorescent β-galactosidase substrates, such as fluoroscein di-β-D-galactopyranside, and products make it very difficult to screen large libraries for both expressing and non-expressing cells because the substrate and product is not well retained or permits ratiometric analysis to determine the amount uncleaved substrate. Green fluorescent protein (GFP), a non-enzymatic reporter, could be used to detect expression in single living cells but has limited sensitivity. GFP expression level would have to be at least 100,000 molecules per cell to be detectable in a screening format and small changes in, or low levels of, gene expression could not be measured. Furthermore GFP is relatively stable and would not be suitable for measuring down-regulation of genes. Other advantages of the invention are described herein or readily recognized by one skilled in the art upon reviewing this disclosure.

Methods for Rapidly Identifying Modulators of Genomic Polynucleotides

The invention provides for a method of identifying proteins or compounds that directly or indirectly modulate a genomic polynucleotide. Generally, the method comprises inserting a BL expression construct into an eukaryotic genome, usually non-yeast, contained in at least one living cell, contacting the cell with a predetermined concentration of a modulator, and detecting BL activity in the cell. Preferably, cleavage of a membrane permeant BL substrate is measured and the membrane permeant BL substrate is transformed in the cell into a trapped substrate. Preferably, the BL expression construct comprises a BL polynucleotide, a splice donor, a splice acceptor and an IRES element. The method can also include determining the coding nucleic acid sequence of a polynucleotide operably linked to the BL expression construct using techniques known in the art, such as RACE.

Modulators described herein can be used in this system to test for an increase or decrease in BL activity in successfully integrated clones. Such cells can optionally include specific proteins of interest as discussed herein. For example, the cell can include a protein or receptor that is known to bind the modulator (e.g. a nuclear receptor or receptor having a transmembrane domain heterologously or homologously expressed by the cell). A second modulator can be added either simultaneously or sequentially to the cell or cells and BL activity can be measured before, during or after such additions. Cells can be separated on the basis of their response to the modulator (e.g. responsive or non-responsive) and can be characterized with a number of different modulators to create a profile of cell activation or inhibition.

BL activity will often be measured in relation to a reference sample, often a control. For example, BL activity is measured in the presence of the modulator and compared to the absence of the modulator or possibly a second modulator. Alternatively, BL activity is measured in a cell expressing a protein of interest and to a cell not expressing the protein of interest (usually the same cell type). For instance, a modulator may be known to bind to a receptor expressed by the cell and the BL activity in the cell is increased in the presence of the modulator compared to the BL activity detected from a corresponding cell in the presence of the modulator, wherein the corresponding cell does not express of the receptor.

In one embodiment, the invention provides for a genomic assay system to identify downstream transcriptional targets for signaling pathways. This method requires the target of interest to activate gene expression upon addition of compound or expression of a the target protein. A cell line that is the most similar to the tissue type where the target functions is preferred for generating a library of clones with different integration sites with BL polynucleotides. This cell line may be known to elicit a cellular response, such as differentiation upon addition of a particular modulator. If this type of cell line is available, it is preferred for screening, as it represents the native context of the target. If a cell line is not available that homologously expresses the target, a cell line can be generated by heterologously expressing the target in the most relevant cell line. For instance, if the target is normally expressed in the lymphoid cells, then a lymphoid cell line would be used generate the library.

The library of clones, as described further herein, would be separated into two pools by FACS using the FRET system described herein: an expressing pool (blue cells) and a non-expressing pool (green cells). These two pools would then be treated with modulator followed by FACS to isolate induced clones (green to blue) or repressed clones (blue to green). Additional rounds of stimulation followed by FACS could be done to verify initial results. The specificity of activation could be tested by adding additional compounds that should not activate the defined target. This would allow the identification of clones that have β-lactamase polynucleotides integrated into genes activated by a variety of cellular signals.

Once a pool of cells with the desired characteristics are isolated they can be expanded and their corresponding genes cloned and characterized. Targets which could be used in this assay system include receptors, kinases, protein/protein interactions or transcription factors and other proteins of interest discussed herein.

In another embodiment, the invention provides for a method of identifying developmentally or tissue specific expressed genes. β-lactamase polynucleotides can be inserted, usually randomly, into any precursor cell such as an embryonic or hematopoetic stem cell to create a library of clones. Constitutively expressing clones can be collected by sorting for blue cells and non-expressing cells collected by sorting for green cells using the FRET system described herein. The library of clones can then be stimulated or allowed to differentiate and induced or repressed clones isolated. Cell surface marker in conjunction with fluorescent tagged antibodies or other detector molecules could be used to monitor the expression of reference genes simultaneously. Additionally, by stimulation and sorting stem cells at various developmental stages, it is possible rapidly identify genes responsible for maturation and differentiation of particular tissues.

Additionally, clones which have a β-lactamase polynucleoitdes integrated, either randomly or by homolgous recombination, into developmentally expressed genes could be used with FACS to isolate specific cell populations for further study. This can be used for identifying cell populations which have stem cells properties and provide an intracellular reporter which allows isolation of this population of cells.

In another embodiment, the invention provides for a method of identifying modulator for orphan proteins or genomic polynucleotides that are directly or indirectly modulated by an orphan protein. Human disease genes are often identified and found to show little or no sequence homology to functionally characterized genes. Such genes are often of unknown function and thus encode for an "orphan protein." Usually such orphan proteins share less than 25% amino acid sequence homology with other known proteins or are not considered part of a gene family. With such molecules there is usually no therapeutic starting point. By using libraries of the herein described clones, one can extract functional information about these novel genes. Orphan proteins can be expressed, preferably, overexpressed in living mammalian cells. By inducing overexpression of the orphan gene and monitoring the effect on specific clones one may identify genes which are transcriptionally regulated by the orphan protein. By identifying genes whose expression is influenced by the novel disease gene or other orphan protein one may predict the physiological bases of the disease or function of the orphan molecule. Insights gained using this method can lead to identification of a valid therapeutic target for disease intervention.

In another embodiment, the invention provides for a method of screening a defined target or modulator using genomic polynucleotides identified with the methods described herein. The gene identification methods described herein can also be used in conjunction with a screening system for any target which functions through transcriptional regulation. For example, a functional analysis screen for a cytokine receptor. In many instance the receptor and its ligand are known but not the downstream biological processes required for signaling. For example, the cytokine receptor and cytokine are known but the downstream signaling mechanism is not. A library of clones generated from a cell line which expresses the cytokine receptor can be screened to identify clones showing changes in gene expression when stimulated by the cytokine. The induced genes could be characterized to describe the signaling pathway. Using the methods of the invention, gene characterization is not required for screen development as identification of a cell clone which specifically responds to the cytokine constitutes a usable secondary screen. Therefore, clones which show activation or deactivation upon the addition of the cytokine can be expanded and used to screen for agonists or antagonists. The advantage of this type of screening is that it does not require an initial understanding of the signaling pathway and is therefore uniquely capable of identifying leads for novel pathways.

In another embodiment, the invention provides for a method of functionally characterizing a target using a panel of clone having active genomic polynucleotides as identified herein. As large numbers of specifically responding cell lines containing active genomic polynucleotides identified with a particular biological process or modulator are generated, panels containing specific clones can be used for functional analysis of other potential cellular modulators. These panels of responding cell lines can be used to rapidly profile potential transcriptional regulators. Such panels, as well as containing clones with identified active genomic polynucleotides, which were generated by the invention panels, can include clones generated by more traditional methods. Clones can be generated that contain both the identified active genomic polynucleotide with a BL polynucleotide and specific response elements, such as SRE, CRE, NFAT, TRE, IRE, or reporters under the control of specific promoters. These panels would therefore allow the rapid analysis of potential effectors and their mechanisms of cellular activation. A second reporter gene can also be used with this method, as well as the other method described herein.

In another embodiment, the invention provides for a method of test compound profiling using a clone or panel of clones having identified active polynucleotides. Test compound characterization is similar to target characterization except that the cellular target(s) do not have to be known. This method will therefore allow the analysis of test compounds (e.g. lead drugs) effects on cellular function by defining genes effected by the drug or drug lead.

Such a method can find application in the area of drug discovery and secondary affects (e.g. cytotoxic affect) of drugs. The potential drug would be added to a library of genomic clones and clones which either were induced or repressed would be isolated. This method is analogous to target characterization except that the secondary drug target is unknown. As well as providing a screen for the secondary effects, the assay provides information on the mechanism of toxicity.

Methods Related to FACS and Identifying Active Genomic Polynucleotides

The invention provides for a method of identifying active genomic polynucleotides using clones having integrated BL polynucleotides and FACS. β-lactamase integration libraries can be used in a high-throughput screening format, such as FACS, to detect transcriptional regulation. The compatibility of β-lactamase assays with FACS enables a systematic method for defining patterns of transcriptional regulation mediated by a range of factors. This approach has not been feasible or practical using existing reporter systems. This new method will allow rapid identification of genes responding to a variety of signals, including tissue specific expression and during pattern formation.

For example, after integration of a β-lactamase polynucleotide, expressing and non-expressing cells will be separated by FACS. These two cell populations can be treated with potential effectors and changes in gene expression monitored using ratio-metric fluorescent readout. Pools of clones will be isolated which show either up- or down-regulation of reporter gene expression. Target genes from responding clones can then be identified. In addition, by being able to separate expressing and non-expressing cells at different time points after effector stimulation, genes which are differentially regulated over time can be identified. This approach therefore enables the elucidation of transcription cascades mediated by cellular signaling. Specifically, it will provide a means to identify downstream genes which are transcriptionally regulated by a variety of molecules including, nuclear receptors, cytokine receptors or transcription factors.

Applications of this technology are nearly unlimited in the areas of gene discovery and functional analysis. Libraries of cell lines from various tissue types could be generated and used as a resource to identify genes with specific expression patterns or regulation mechanisms. These libraries of clones would represent millions of integration sites saturating the genome and would permit the identification of any expressed gene based on its transcriptional regulation. The features of the β-lactamase reporter system, in part, allow its use for this genomic integration assay in a high-throughput format. Although various assays have been widely used for the identification of developmentally expressed genes, this is the first use of a genomic integration assay in drug discovery.

There are a variety of other approaches which may be used with the invention, including approaches similar to those proposed for β-lactamase. Examples would include antibody epitopes presented on the cell surface with fluorescent antibodies to detect positive cells. Gel matrixes could also be used which retain secreted reporters and allow detection of positive cells. These approaches would, however, be limited in sensitivity and would not be ratio-metric in their detection. They would therefore allow for only the sorting of positive cells based on fluorescent intensity.

Once active genomic polynculeotides have been identified, they can be sequences using various methods including RACE. Rapid amplification of cDNA ends (RACE) is a procedure for the identification of unknown mRNA sequences which flank known mRNA sequences. Both 5' and 3' ends can be identified depending of the RACE conditions. 5' RACE is done by first preparing RNA from a cell line or tissue of interest. This total or polyA RNA is then used as a template for a reverse transcription reactions which can either be random primed or primed with a gene-specific primer. A poly nucleotide linker of known sequence is then attached to the 3' end of the newly transcribed cDNA by terminal transferase or RNA ligase. This cDNA is then used as the template for PCR using one primer within the gene of interest and the other primer corresponding to sequence which had been linked to the 3' end of the first stand cDNA. The present invention is particularly well suited for such techniques and does not require construction of additional clones or constructs once the genomic polynucleotide has been identified.

Substrates for Measuring BL activity

Any membrane permanent BL substrate capable of being measured inside the cell after cleavage can be used in the methods and compositions of the invention. Membrane permanent BL substrates will not require permeablizing eukaryotic cells either by hypotonic shock or by electroporation. Generally, such non-specific pore forming methods are not desirable to use in eukaryotic cells because such methods injure the cells, thereby decreasing viability and introducing additional variables into the screening assay (such as loss of ionic and biological contents of the shocked or porated cells). Such methods can be used in cells with cell walls or membranes that significantly prevent or retard the diffusion of such substrates. Preferably, the membrane permeant BL substrates are transformed in the cell into a BL substrate of reduced membrane permeability (usually at least five less permeable) or that is membrane impermeant. Transformation inside the cell can occur via intracellular enzymes (e.g. esterases) or intracellular metabolites or organic molecules (e.g. sulfhydryl groups). Preferably, such substrates are fluorescent. Fluorescent substrates include those capable of changes, either individually or in combination, of total fluorescence, excitation or emission spectra or FRET.

Preferably, FRET type substrates are employed with the methods and compositions of the invention. Including fluorogenic substrates of the general formula I:

D-S-A wherein D is a FRET donor and A is an FRET acceptor and S is a substrate for a protein with BL activity. BL activity cleaves either D-S or S-A bonds thereby releasing either D or A, respectively from S. Such cleavage resulting from BL activity dramatically increases the distance between D and A which usually causes a complete loss in energy transfer between D and A. Generally, molecules of D-S-A structure are constructed to maximize the energy transfer between D and A. Preferably, the distance between D and A is generally equal to or less than the $R_o$.

As would readily be appreciated by those skilled in the art, the efficiency of fluorescence resonance energy transfer depends on the fluorescence quantum yield of the donor fluorophore, the donor-acceptor distance and the overlap integral of donor fluorescence emission and acceptor absorption. The energy transfer is most efficient when a donor fluorophore with high fluorescence quantum yield (preferably, one approaching 100%) is paired with an acceptor with a large extinction coefficient at wavelengths coinciding with the emission of the donor. The dependence of fluorescence energy transfer on the above parameters has been reported [Forster, T. (1948) *Ann. Physik* 2: 55–75; Lakowicz, J. R., *Principles of Fluorescence Spectroscopy*, New York: Plenum Press (1983); Herman, B., Resonance energy transfer microscopy, in: *Fluorescence Microscopy of Living Cells in Culture, Part B, Methods in Cell Biology*, Vol 30, ed. Taylor, D. L. & Wang, Y.-L., San Diego: Academic Press (1989), pp. 219–243; Turro, N.J., *Modern Molecular Photochemistry*, Menlo Part: Benjamin/Cummings Publishing Co., Inc. (1978), pp. 296–361], and tables of spectral overlap integrals are readily available to those working in the field [for example, Berlman, I. B. *Energy transfer parameters of aromatic compounds*, Academic Press, New York and London (1973)]. The distance between donor fluorophore and acceptor dye at which fluorescence resonance energy transfer (FRET) occurs with 50% efficiency is termed $R_0$ and can be calculated from the spectral overlap integrals. For the donor-acceptor pair fluorescein-tetramethyl rhodamine which is frequently used for distance measurement in proteins, this distance $R_0$, is around 50–70 A [dos Remedios, C. G. et al. (1987) *J. Muscle Research and Cell Motility* 8:97–117]. The distance at which the energy transfer in this pair exceeds 90% is about 45 A. When attached to the cephalosporin backbone the distances between donors and acceptors are in the range of 10 A to 20 A, depending on the linkers used and the size of the chromophores. For a distance of 20 A, a chromophore pair will have to have a calculated $R_0$ of larger than 30 A for 90% of the donors to transfer their energy to the acceptor, resulting in better than 90% quenching of the donor fluorescence. Cleavage of such a cephalosporin by b-lactamase relieves quenching and produces an increase in donor fluorescence efficiency in excess of tenfold. Accordingly, it is apparent that identification of appropriate donor-acceptor pairs for use as taught herein in accordance with the present invention would be essentially routine to one skilled in the art.

Other FRET type substrates are more preferred and of the general formula II:

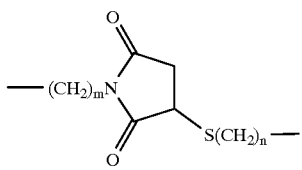

in which one of X and Y is a fluorescent donor moiety and the other is a quencher (which may or may not re-emit); R' is selected from the group consisting of H, lower alkyl, $(CH_2)_nOH, (CH_2)_nCOOR''$, and $=NOJ$, in which n is 0 or an integer from 1 to 5 and J is H, Me, $CH_2COOH$, $CHMeCOOH$, and $CMe_2COOH$; R'' is selected from the group consisting of H, physiologically acceptable metal and ammonium cations, $-CHR^2OCO(CH_2)_nCH_3$, $-CHR^2OCOC(CH_3)_3$, acylthiomethyl, acyloxy-alpha-benzyl, delta-butyrolactonyl, methoxycarbonyloxymethyl, phenyl, methylsulphinylmethyl, beta-morpholinoethyl, dialkylaminoethyl, and dialkylaminocarbonyloxymethyl, in which $R^2$ is selected from the group consisting of H and lower alkyl; A is selected from the group consisting of S, O, SO, $SO_2$ and $CH_2$; and Z' and Z'' are linkers for the fluorescent donor and quencher moieties.

The linkers Z' and Z'' serve the purpose of attaching the fluorescent donor and quencher moieties to the cephalosporin-derived backbone, and may facilitate the synthesis of the compounds of general formula I. In general formula I, Z' may represent a direct bond to the backbone; alternatively, suitable linkers for use as Z' include, but are not limited to, the following: $-(CH_2)_nCONR^2(CH_2)_m-$, $-(CH_2)_nNR^2CO(CH_2)_m-$, $-(CH_2)_nNR^3CONR^2(CH_2)_m-$, $-(CH_2)_nNR^3CSNR^2(CH_2)_m-$, $-(CH_2)_nCONR^3(CH_2)_pCONR^2(CH_2)_m-$, $-(CH_2)_n-$, $-(CH_2)_nNR^3CO(CH_2)_pS(CH_2)_m-$, $-(CH_2)_nS(CH_2)_m-$, $-(CH_2)_nO(CH_2)_m-$, $-(CH_2)_nNR^2(CH_2)_m-$, $-(CH_2)_nSO_2NR^2(CH_2)_m-$, $-(CH_2)_nCO_2(CH_2)_m-$,

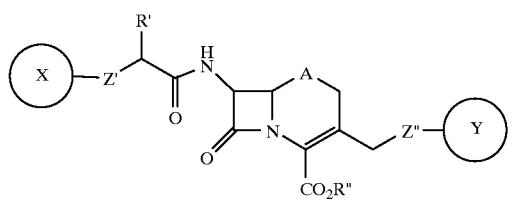

and

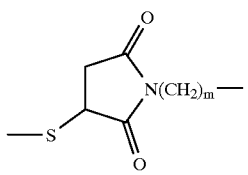

wherein $R^2$ and n are as previously defined; $R^3$ is selected from the group consisting of hydrogen and lower alkyl; and each of m and p is independently selected from the group consisting of 0 and integers from 1 to 4. Especially preferred are Z' groups such where n and m are 0. Also particularly preferred are such Z' groups where $R^2$ is H.

Suitable linkers Z'' for the Y moiety include, but are not limited to, a direct bond to a heteroatom (e.g., O, N or S) in the dye's chromophore or the following: $-O(CH_2)_n-$, $-S(CH_2)_n-$, $-NR^2(CH_2)_n-$, $-N^+R^2{}_2(CH_2)_n-$, $-OCONR^2(CH_2)_n-$, $-O_2C(CH_2)_n-$, $-SCSNR^2(CH_2)_n-$, $-SCSO(CH_2)_n-$, $-S(CH_2)_nCONR^2(CH_2)_m$, $-S(CH_2)_nNR^2CO(CH_2)_m$, and

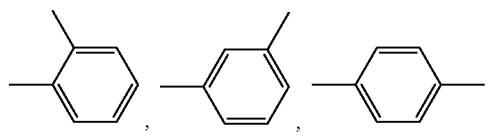

in which $R^2$, n and m are as previously defined; and m is an integer from 0 to 4. Particularly preferred Z'' groups are $-S(CH_2)_n$. Especially preferred is H.

Preferred R' groups include H and methyl. Particularly preferred is H. Preferred R'' groups include H and acetoxymethyl. A preferred $R^2$ group is H. A preferred A group is $-S-$.

In a preferred aspect, the compounds of the present invention are membrane-permeant. Particularly preferred are such compounds wherein at least one of X and Y contains at least one acylated aromatic hydroxyl, acylated amine, or alkylated aromatic hydroxyl wherein the acyl group contains 1 to 5 carbon atoms and wherein the alkyl group is selected from the group consisting of $-CH_2OC(O)alk$, $-CH_2SC(O)alk$, $-CH_2OC(O)Oalk$, lower acyloxy-alpha-benzyl, and delta-butyrolactonyl, wherein alk is lower alkyl of 1 to 4 carbon atoms. Particularly preferred are such compounds where at least one of X and Y contains at least one acylated aromatic hydroxy, wherein the acyl group is either acetyl, n-propionyl, or n-butyryl. Also particularly preferred are such compounds wherein at least one of X and Y contains an acetoxy methyl group on an aromatic hydroxyl group.

To measure b-lactamase activity in the cytoplasm of living cells, smaller molecular weight chromophores as hereinafter described are in general preferred over larger ones as substrate delivery becomes a problem for larger compounds. Large molecules, especially those over about 1200 daltons, also tend to bind more avidly to cellular constituents than small ones, thereby removing at least some of them from access and cleavage by b-lactamase.

Fluorescence Measurements

When using fluorescent substrates, it will recognized that different types of fluorescent monitoring systems can be used to practice the invention. Preferably, FACS systems are used or systems dedicated to high throughput screening, e.g 96 well or greater microtiter plates. Methods of performing assays on fluorescent materials are well known in the art and are described in, e.g., Lakowicz, J. R., *Principles of Fluorescence Spectroscopy*, New York: Plenum Press (1983); Herman, B., Resonance energy transfer microscopy, in: *Fluorescence Microscopy of Living Cells in Culture, Part B, Methods in Cell Biology*, vol. 30, ed. Taylor, D. L. & Wang, Y.-L., San Diego: Academic Press (1989), pp. 219–243; Turro, N.J., *Modern Molecular Photochemistry*, Menlo Park: Benjamin/Cummings Publishing Col, Inc. (1978), pp. 296–361.

Fluorescence in a sample can be measured using a fluorimeter. In general, excitation radiation, from an excitation source having a first wavelength, passes through excitation optics. The excitation optics cause the excitation radiation to excite the sample. In response, fluorescent proteins in the sample emit radiation which has a wavelength that is different from the excitation wavelength. Collection optics then collect the emission from the sample. The device can include a temperature controller to maintain the sample at a specific temperature while it is being scanned. According to one embodiment, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

Preferably, FRET is used as a way of monitoring BL activity inside a cell. The degree of FRET can be determined by any spectral or fluorescence lifetime characteristic of the excited construct, for example, by determining the intensity of the fluorescent signal from the donor, the intensity of fluorescent signal from the acceptor, the ratio of the fluorescence amplitudes near the acceptor's emission maxima to the fluorescence amplitudes near the donor's emission maximum, or the excited state lifetime of the donor. For example, cleavage of the linker increases the intensity of fluorescence from the donor, decreases the intensity of fluorescence from the acceptor, decreases the ratio of fluorescence amplitudes from the acceptor to that from the donor, and increases the excited state lifetime of the donor.

Preferably, changes in the degree of FRET are determined as a function of the change in the ratio of the amount of fluorescence from the donor and acceptor moieties, a process referred to as "ratioing." Changes in the absolute amount of substrate, excitation intensity, and turbidity or other background absorbances in the sample at the excitation wavelength affect the intensities of fluorescence from both the donor and acceptor approximately in parallel. Therefore the ratio of the two emission intensities is a more robust and preferred measure of cleavage than either intensity alone.

The excitation state lifetime of the donor moiety is, likewise, independent of the absolute amount of substrate, excitation intensity, or turbidity or other background absorbances. Its measurement requires equipment with nanosecond time resolution, except in the special case of lanthanide complexes in which case microsecond to millisecond resolution is sufficient.

The ratio-metric fluorescent reporter system described herein has significant advantages over existing reporters for gene integration analysis, as it allows sensitive detection and isolation of both expressing and non-expressing single living cells. This assay system uses a non-toxic, non-polar fluorescent substrate which is easily loaded and then trapped intracellularly. Cleavage of the fluorescent substrate by β-lactamase yields a fluorescent emission shift as substrate is converted to product. Because the β-lactamase reporter readout is ratiometric it is unique among reporter gene assays in that it controls for variables such as the amount of substrate loaded into individual cells. The stable, easily detected, intracellular readout eliminates the need for establishing clonal cell lines prior to expression analysis. With the β-lactamase reporter system or other analogous systems flow sorting can be used to isolate both expressing and non-expressing cells from pools of millions of viable cells. This positive and negative selection allows its use with gene identification methods to isolate desired clones from large clone pools containing millions of cells each containing a unique integration site.

EXAMPLES

Example 1

To investigate various beta-lactamase expression constructs (BLECs) multiple BLECs were constructed and transfected into mammalian cells.

Figure 2:
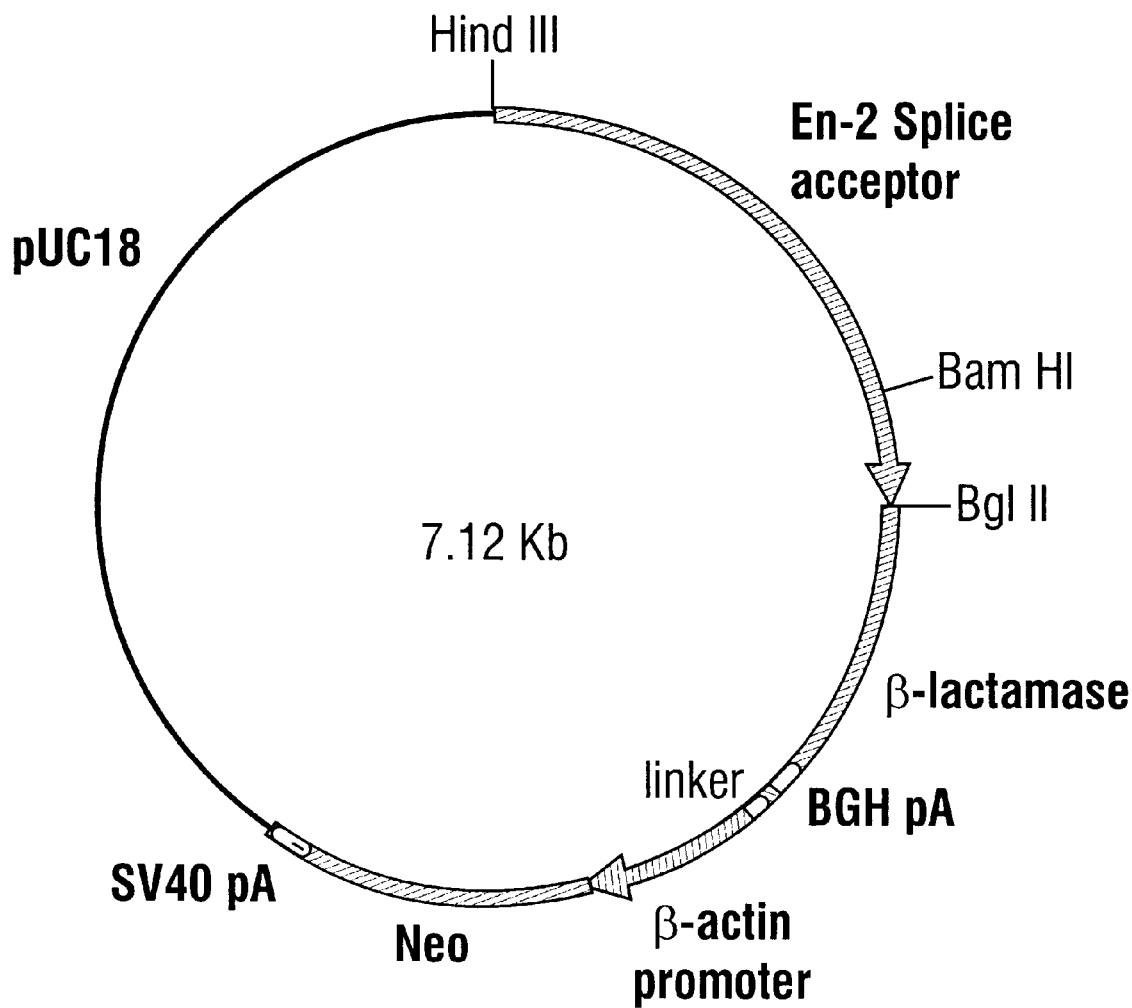
FIG. 2 shows a schematic plasmid map of the BLEC-1.

The first of these, BLEC-1 was constructed by cloning the cytoplasmic form of BL SEQ. ID NO. 4 (see Table 1) such that it is functionally linked to the En-2 splice acceptor sequence, as shown in FIG. 2. This vector when inserted into a genomic intron will result in the generation of a fusion RNA between an endogenous target gene and BL. BLEC-1 also contains a bovine growth hormone poly-adenlyation sequence (BGH-polyA) downstream of the cytoplasmic Beta-lactamase.

BLEC-2 was constructed identically to BLEC-1, except that a poliovirus internal ribosomal entry site (IRES) sequence was inserted between the En-2 splice acceptor BL. This eliminates reading frame restrictions and possible inactivation of beta-lactamase by fusion to an endogenous protein. To allow for selection of stable transfectants for BLEC-1 and BLEC-2 a neomycin or G418 resistance cassette was cloned downstream of the BGH poly-adenylation sequence. This cassette consists of a promoter, neomycin resistance gene and an SV40 poly-adenylation sequence, as shown in FIG. 2.

Two alternative constructs BLEC-3 and BLEC-4 were constructed similar to BLEC-1, and BLEC-2 respectively, except the SV40-poly A was replaced with a splice donor sequence. This should enrich for insertion into transcribed regions as it requires the presence of an endogenous splice acceptor and polyadenylation sequence downstream of the vector insertion site to generate G418 resistant clones. BLEC-3 and BLEC-4 also use the PGK promoter to drive the neomycin resistance gene instead of the human beta-actin promoter.

The structure of CCF2-AM (BL substrate) used in the experiments below is:

TABLE 1

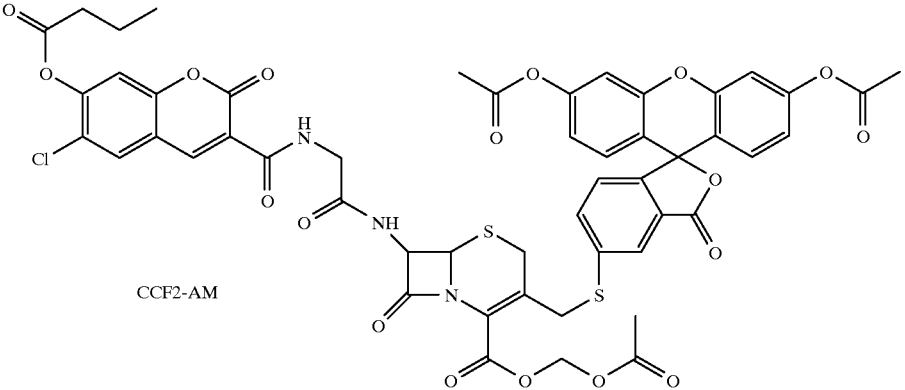

CCF2-AM

| SEQ. ID NO. | parent -BL gene and reference | modification | mammalian expression vector | location of expression |
|---|---|---|---|---|
| #1 | *Escherichia coli* RTEM Kadonaga et al. | Signal sequence replaced by: ATG AGT | pMAM-neo glucocorticoid-inducible | cytoplasmic |
| #2 | *Escherichia coli* RTEM Kadonaga et al. | Wild type secreted enzyme 2 changes in pre-sequence: ser 2 arg , ala 23 gly | pMAM-neo glucocorticoid-inducible | secreted extracellularly |
| #3 | *Escherichia coli* RTEM | -globin up stream leader: AAGCTTTTTGCAGAAGCTCA GAATAAACGCAACTTTCCG Kozak sequence: GGTACCACCATGG signal sequence replaced by: ATG GGG | pCDNA 3 CMV promotor and pZEO SV40 promotor | cytoplasmic |
| #4 | *Escherichia coli* RTEM | Kozak sequence: GGTACCACCATGG signal sequence replaced by: ATG GAC (GAC replaces CAT) | pCDNA3 CMV promoter AND BLECs | cytoplasmic |
| #5 | *Bacillus licheniformis* 749/C Neugebauer et al. | signal sequence removed, new N-terminal ATG | pCDNA 3 CMV promotor | cytoplasmic |

TABLE 2

Functional Elements

| VECTORS | Splice acceptor | Adapter | Reporter gene | Reporter gene poly A | Selection Promoter | Resistant Marker poly A |
|---|---|---|---|---|---|---|
| BLEC-1 | En2-splice acceptor | Protein fusion | SEQ. ID NO. 4 | BGH polyA | β-actin promoter | Neo polyA |
| BLEC-2 | En2-splice acceptor | IRES | SEQ. ID NO. 4 | BGH polyA | β-actin promoter | Neo-polyA |
| BLEC-3 | En2-splice acceptor | Protein fusion | SEQ. ID NO. 4 | BGH polyA | PGK promoter | Neo-splice donor |
| BLEC-4 | En2-splice acceptor | IRES | SEQ. ID NO. 4 | BGH polyA | PGK promoter | Neo-splice donor |

Example 2

To investigate the function of each of the BLEC vectors they were transfected by electroporation into RBL-1 cells and stable clones were selected for each of the four BLEC plasmids (see Table 2). Selective media contained DMEM, 10% fetal bovine serum (FBS) and 400 μg/ml Geneticin (G418). G418 resistant cell clones were pooled from multiple transfections to generated a library of BLEC stable integrated clones.

This library of BLEC-1 integrated clones was loaded with the fluorescent substrate of BL (CCF-2-AM) by adding 10 μM CCF-2-AM in HBSS containing 10 μM hepes 7.1 and 1% glucose. After a 1 hour incubation at 22° C. cells were washed with HBSS and viewed upon excitation with 400 nm light using a 435 nm long pass emission filter. Under these assay conditions 10% of the cells were blue fluorescent indicating they were expressing β-lactamase. This results suggests that that BLEC-1 construct is functioning as a gene integration vector.

Stable cell lines were also generated by transfecting BLEC-1 into CHO-K1 and Jurkat cells. Populations of BLEC-1 integrated clones from CHO and Jurkat cells showed similar results to those obtained with RBL-1 clones with 10–15% of BLEC integrated cell clones expressing BL as determined by their blue/green ratio after loading with CCF-2-AM. This result shows that the BLECs function in a variety of cell types including human T-cells (Jurkat), rat basophilic leukocytes (RBL), and Chinese hamster ovarian (CHO).

Example 3

Figure 3A:
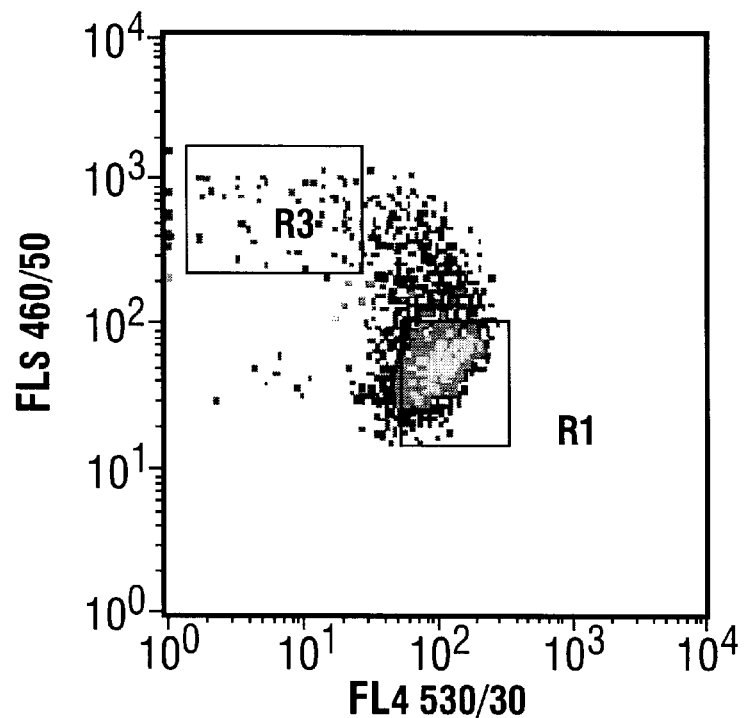
FIG. 3, Panels A–C show the FACS analysis of a population of genomically BLEC integrated clones. Individually cells are plotted by fluorescent emission properties at 400 nm excitation. The x axis represents green emission (530 nm). The y axis represents blue emission (465 nm). Cells with a high blue/green ration will appear blue in color and cells with a low blue/green ratio will appear green in color. A) Unselected multiclonal population of BLEC integrated RBL-1 cell clones. B) Population of clones sorted from 3A (R1) that were cultured for an additional 7 days and resorted. C) Population from 3B with addition of 1 uM ionomycin for 12 hours prior to sorting.
Figure 3B:
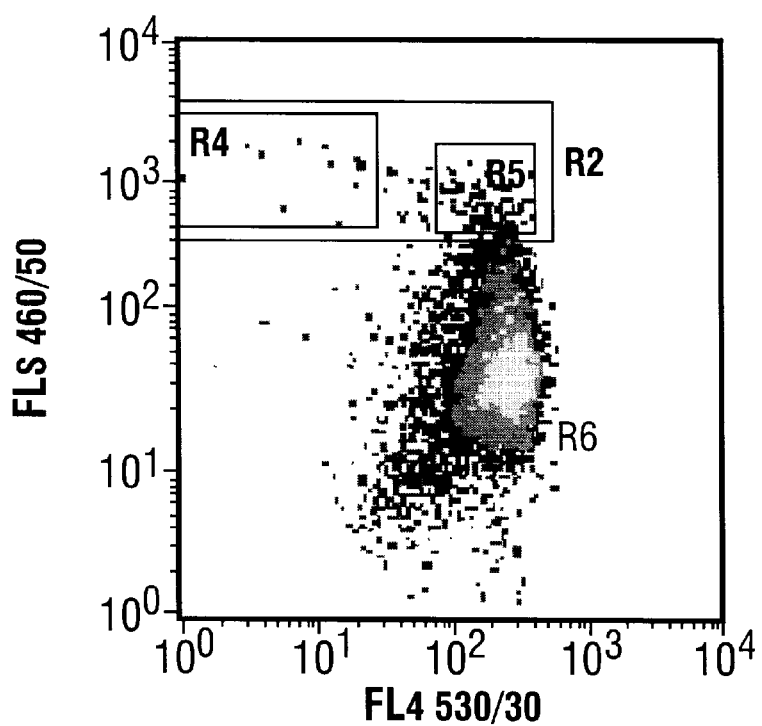

Fluorescent activated cell sorting of multi-clonal populations of RBL-1 gene integrated clones was used to identify clones with regulated BL gene expression. A BL non-expressing population of cells was isolated by sorting a library of BLEC-1 integrated clones generated by transfection of RBL-1 cells as described in Example 2. 180,000 clones expressing little or no BL were isolated by sorting for clones with a low blue/green ratio (R1 population), as shown in FIG. 3A. This population of clones was grown for seven days and resorted by FACS to test the population's fluorescent properties. FACS analysis of the cell clones sorted from R1 shows that most of the cells with a high blue/green ratio ~0.1% have been removed by one round of sorting for green cells, as shown in FIG. 3B. It is also clear that the total population has shifted towards more green cells compared to the parent population, as shown in FIG. 3A. There are, however, cells with a high blue/green ratio showing up in the green sorted population. These may represent clones in which the BLEC has integrated into a differentially regulated gene such as a gene whose expression changes throughout the cell cycle.

The population of RBL-1 clones shown in FIG. 3B was stimulated by addition of 1 uM ionomycin for 6 hours and resorted to identify clones which had the BLEC integrated into a gene which is inducible by increasing intracellular calcium. Table 3 below summarizes the results from this experiment. A greater percentage of blue clones were present in all three of the blue sub-population (R4, R2, R5) in the ionomycin stimulated when compared to the unstimulated population. These sorted population represent the following classes of blue cells: R4 (highest blue/green ratio (bright blues)), R2 (multicolor blues), R5 (lower blue/green ratio (least blue)). Additionally, in the ionomycin stimulated population there is a decrease in the percent green cells from the unstimulated population (R6). This increase in blue clones in the ionomycin stimulated population indicates that a sub-population of blue clones have the BLEC inserted into a gene which is induced by ionomycin. Individual blue clones were sorted from the ionomycin stimulated population and are analyzed for their expression profile.

TABLE 3

Figure 3C:
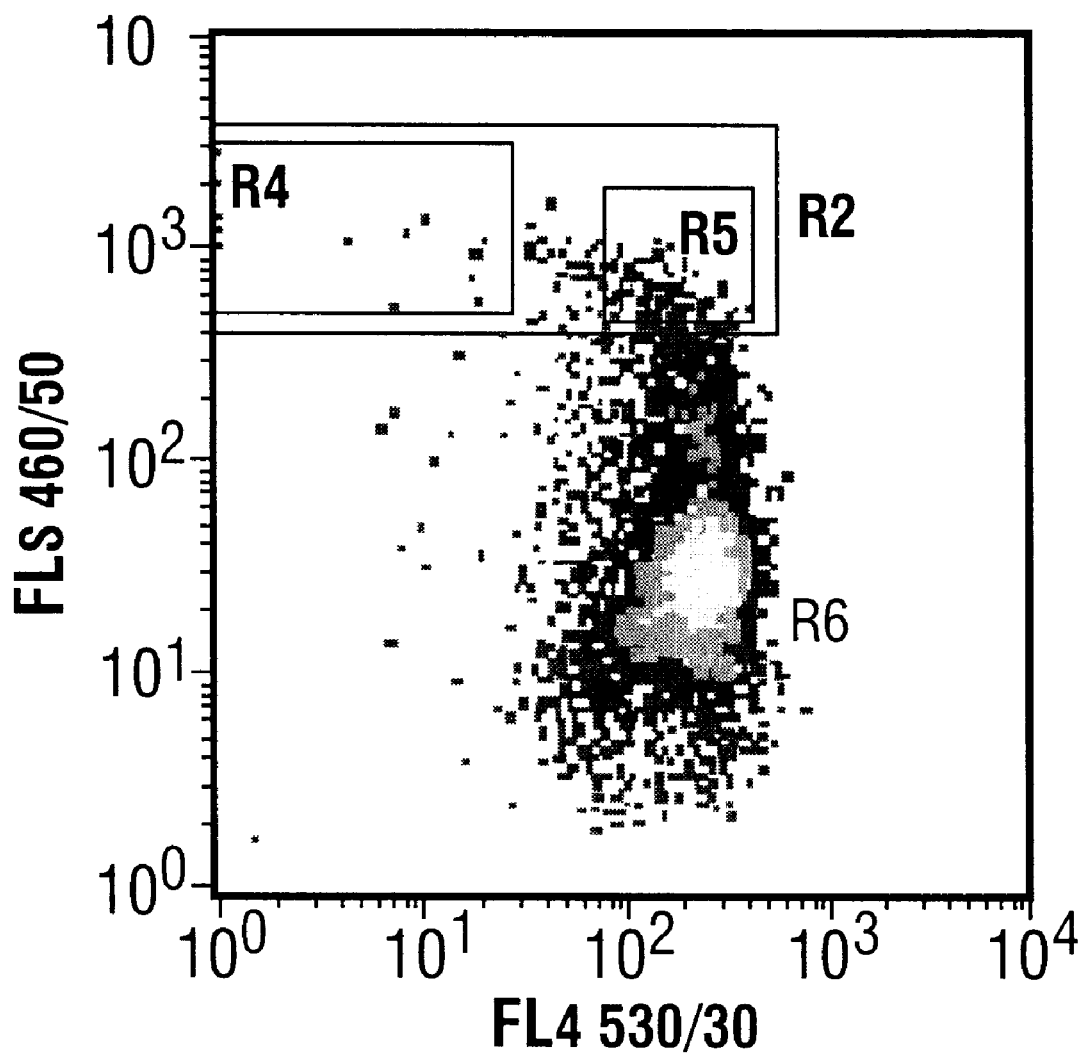

| | Sort Window (See FIG. 3) | | | |
|---|---|---|---|---|
| | R4 (blue) | R2 | R5 | R6 (green) |
| Unstimulated % | .11 | 2.39 | 1.53 | 66.23 |
| 1uM Ionomycin Stimulated % | .24 | 3.5 | 2.5 | 61.64 |
| Ratio +Ion/−Ion | 2.2 | 1.5 | 1.6 | .9 |

In addition to allowing the isolation of cell clones with inducible BL expression from large populations of cells, clones can be isolated based their level of BL expression. To isolate cells with different levels of BL expressions blue clones can be sorted after different exposure times to substrate or by their blue/green ratio. Cell with a lower blue/green ratio or those requiring longer incubation times will represent clones expressing lower levels of BL. This is demonstrated by the FACS scan above as clones sorted from the R4 window have a higher blue/green ration indicating they are expressing higher levels of BL, cells sorted from the R5 have a lower blue/green ratio (visually turquoise) indicating lower BL expression. Cell sorted from the R3 window which contain all the blue cells show variation in blue color from bright blue (high blue/green ratio) to turquoise blue (low blue/green ratio).

To demonstrate that the expression constructs are relatively stable for sorted clones cells were sorted from R3 (blue population) as shown in FIG. 3A and cultured in the absence of selective pressure for several weeks. There was little change in the percent of blue cells in the cultured population with the percent blue being maintained at ~90%. This results represents a 10 fold enrichment for clones constitutively expressing BL by one round of FACS selection.

Cells in R6 window have the lowest blue/green ration and appear green visually. R6 cell are therefore not expressing BL or are expressing BL below the detection limit of our assay.

Example 4

To further investigate the stability of reporter gene integrations into constitutively active genes, single blue clones were sorted from cell clone populations generated by transfecting RBL-1, and CHOK1 with BLEC-1. After addition of CCF-2 to the multi-clonal cell population, single blue clones were sorted into 96 well microtiter plates. These clones were expanded to 24 well dishes which took 7–10 days. The cell viability varied between the two cell types with 80% of the sorted clones forming colonies for the CHO and 36% for the RBL-1 cells. After expansion into a 24 well dishes 20 CHO BLEC-1 stable clones were tested for BL expression by addition of CCF-2-AM. 20/20 of these clones expressed BL with the percent blue cells within a clone ranging from 70% to 99%. This result is consisted with the earlier data presented for RBL-1 in which the blue sorted population was tested for BL expression after several weeks of non-selective culturing. There was however a significant differences between clones in their blue/green ratio and hence their level of BL expression. This suggested that genes with different levels of constitutive expression had been tagged with the BLEC. Although there was a significant differences in blue color between separate clones the blue fluorescence within a clone was consistently similar as would be expected in a clonal population. There were however green cells within the blue sorted clones which may indicate that there is some loss of the BLEC-1 plasmid integration site when clones are grown up from a single cell.

Single clones were expanded and used to make RNA for RACE to identify the target gene and DNA for southern analysis.

Example 5

Measurement of activation of an intracellular receptor: Activation of the intracellular glucocorticoid receptor was measured by its ability to upregulate the transcriptional activity of the glucocorticoid responsive element in the mouse mammary tumor virus promotor. This response to steroids was detected as increased intracellular β-lactamase activity on the substrate CCF2-AM causing an appropriate change in fluorescent signal.

The gene for plasmid encoded RTEM β-lactamase of *Escherichia coli* without a signal sequence (SEQ. ID. NO.: 1) was put under transcriptional control of the mouse mammary tumor virus promotor and introduced into a mammalian expression vector. This vector also carried the chloramphenicol resistance marker for amplification of the plasmid in bacteria and the neomycin resistance marker for mammalian selection. It was introduced into baby hamster kidney (BHK) cells in culture using the calcium phosphate precipitation technique. Cells were then subjected to selection for stable integration of the plasmid into the cells' genome using the antibiotic G418. One of twenty clones was selected for its marked increase in β-lactamase expression following exposure to the steroid analog dexamethasone.

The following describes the measurement of the increase in β-lactamase gene expression in this clone after addition of the agonist dexamethasone. Cells of the stable BHK cell clone G941 expressing β-lactamase under control of the glucocorticoid-inducible promotor were kept in the presence or absence of the agonists in the incubator at 37° C. Flasks with cells were removed from the incubator at different intervals after agonist addition and the cells transferred into Hank's balanced salt solution containing 10 μmolar CCF2/btAMac$_2$. This compound becomes converted to the β-lactamase accessible fluorescent substrate CCF2 by endogenous cytoplasmic esterases. Ten minutes later the cell supernatant containing CCF2/btAMac$_2$ was removed. 30 Minutes later the cells were imaged with a cooled CCD camera mounted on an epi-fluorescence microscope. Fluorescence measurements were taken with violet excitation light (filter 400DF15) and with blue (filter 450DF65) and green (filter 535DF45) emission filters. A ratio of blue versus green emission intensities was determined. The ratio is a measure of how much substrate has been converted to product. Using a 40× objective, 4 fields with approximately 60 cells each were imaged at each time point. The results show a significant increase in the ratio of fluorescent intensities reflective of increasing β-lactamase expression and production.

| time in presence of 1 μM dexamethasone | 0.0 hours | 1.0 hours | 2.0 hours | 3.3 hours |
|---|---|---|---|---|
| average ratio of fluorescence intensities 450DF65 / 535DF45 | 0.21 +/− 0.02 | 0.38 +/− 0.05 | 0.42 +/− 0.07 | 0.47 +/− 0.08 |

Example 6

Measurement of cell surface receptor activation and intracellular signaling via second-messenger responsive elements: Activation of cell surface receptors leads to a change in intracellular messenger concentrations which in turn modulates intracellular transcription factor activity. In lymphocytes, an increase the intracellular concentration of the messenger ion calcium leads to the activation of the nuclear factor of activated T-lymphocytes (NFAT). This event increases transcription at promoters containing the NFAT-recognition site. An increase in calcium levels alone is sufficient to markedly increase transcription of a reporter gene such as β-lactamase regulated when it is put under transcriptional control of a promotor containing a trimer of NFAT sites.

The murine T-lymphocyte cell line B3Z was transiently cotransfected with two plasmids. One plasmid contained the β-adrenergic receptor, which localizes at the cells' surface, under the transcriptional control of the strong and constitutively active cytomegalovirus (CMV) promoter. The other plasmid contained the bacterial RTEM β-lactamase gene from Escherichia coli modified for improved mammalian expression (SEQ. ID. NO.: 3, with optimum mammalian Kozak sequence, β-globin leader sequence, pre-sequence removed) under the transcriptional control of a promotor containing a trimer of NFAT sites. The plasmids were introduced into cells using electroporation. 5×10$^6$ cells in 0.5 ml electroporation buffer were electroporated in the presence of 10 μg each of both plasmids using the Biorad Gene Pulser (250V, 960 μF, 16 μsec). Twenty-four hours after transfection, cells were either incubated in the presence or absence of the β-adrenergic agonist isoproterenol (10 μmolar) for 5 hours. The supernatant was removed and replaced with Hank's balanced salt solution containing 10 μmolar CCF2/btAMac$_2$. After 20 minutes at room temperature cells were washed with fresh buffer and viewed with the fluorescence microscope. 4% of isoproterenol treated cells appeared fluorescent blue (excitation filter 400DF15, emission filter 435 nm longpass) while no blue fluorescent cells were detectable in the control population (absence of agonist). Maximal stimulation with 2 μM ionomycin and 50 ng/ml phorbol ester for 5 hours resulted in 20% blue fluorescent cells in the population.

Example 7

β-Lactamases from different microorganisms were modified for use as reporter enzymes in eukaryotic cells, preferably mammalian. The bacterial gene for these enzymes includes a N-terminal pre-sequence (first 23 amino acids of Sequence 2 of FIG. 7.) that targets the enzyme to the extracellular space. Following translocation a pre-sequence peptidase cleaves the 23 amino acid pre-sequence releasing the mature β-lactamase enzyme. RTEM β-lactamase from Escherichia coli including its bacterial pre-sequence (SEQ. ID. NO.2) was put into a mammalian expression vector under the control of the mouse mammary tumor virus promotor. This construct was introduced into baby hamster kidney cells using the standard calcium phosphate precipitation technique. The β-lactamase activity was found in the cell culture medium; no activity could be detected in the cell pellet. The amount of β-lactamase activity in the medium was steroid dependent. Cells that had been in the presence of 1 μM dexamethasone for 36 hours prior to the measurement produced threefold more enzyme than control. This makes the β-lactamase with its bacterial pre-sequence (SEQ. ID. NO.: 2) useful for an extracellular assay of mammalian reporter gene activity.

A preferred use of the β-lactamase reporter is where the enzyme is produced and retained in the cell cytoplasm. Therefore the bacterial signal sequence was removed and replaced by ATG (methionine) as the new translational start site in three modified RTEM β-lactamase genes (SEQ. ID. NO.: 1, 3, 4, and 5). In order to increase expression of the β-lactamases in mammalian cells, the RTEM β-lactamases of SEQ. ID. NO.: 3 and 4 were constructed with altered ribosome binding sites optimized for mammalian expression [Kozak, M., J. Cell Biol. 108: 229–241 (1989)]. For increased compatibility with the mammalian translation machinery, β-lactamase of SEQ. ID. NO.: 3 was inserted at the end of an untranslated mammalian β-globin leader sequence. All of these novel DNA sequences encoding novel β-lactamases were inserted into mammalian expression vectors with the cytomegalovirus promotor controlling their transcription. Mammalian cells in tissue culture (Hela, COS-7, CHO, BHK) were transfected transiently with the plasmids using the standard lipofectin technique. Two to five days after transfection, the cells were incubated with the membrane-permeant derivative, CCF2/btAMac$_2$, of the fluorescent substrate CCF2-AM to assay functional expression of the enzyme. 5–20% of cells transfected with plasmids containing cDNA SEQ. ID. NO.: 1, 3, 4, and 5 showed a conversion of green to blue fluorescence indicating cleavage of the intracellularly trapped substrate by expressed β-lactamase. By contrast, in untransfected or mock transfected controls, all cells showed the green fluorescence of uncleaved CCF2; no blue-fluorescing cells were observed, confirming the absence of any endogenous β-lactamase activity.

The gene for Bacillus licheniformis β-lactamase was isolated from total Bacillus licheniformis DNA by use of the polymerase chain reaction. The oligonucleotide primers removed the β-lactamase secretion sequence and generated the DNA SEQ. ID. NO.: 5. This gene was inserted in a pCDNA3 mammalian expression vector under the transcriptional control of the constitutively active cytomegalovirus promoter. HeLa cells were transfected with 10 μg of plasmid per 25 cm² culture dish using lipofectin. 5 days after transfection, cells were tested for functional expression of β-lactamase by incubating them in the presence of 100 μmolar CCF2/btAMac₂ (CCF2-AM) and visual inspection with the epifluorescence microscope. 30–40% of cells showed blue fluorescence, whereas only green-fluorescing cells, no blue-fluorescing cells were detectable in untransfected controls. In transient transfections, it is typical for <50% of the cells to become transfected.

Example 8

A plasmid was constructed with β-lactamase of SEQ. ID NO.: 3 under control of yeast elongation factor EF-1alpha enhancer and promoter. This plasmid was coinjected together with the potassium salt of substrate CCF2 into zebrafish embryos at the single cell stage. As control, embryos were injected with the potassium salt of substrate CCF2 alone. After three hours, the embryos were viewed with an epifluorescence microscope using violet excitation light (filter 400DF15) and a 435 nm longpass emission filter. Embryos that had received plasmid DNA fluoresced blue while controls fluoresced green.

Example 9

The β-lactamase gene of SEQ. ID. NO.: 3 was cloned into a Drosophila transformation vector under the control of the glass promotor and injected into wild-type Drosophila embryos. As control, the β-lactamase gene was inserted in the wrong orientation. Drosophila embryos were germline-transformed using P element-mediated transformation. The transformations and all subsequent fly manipulations were performed using standard techniques [Karess, R. E. and Rubin, G. M., *Cell* 38, 135, (1984)]. Omatidia of late stage transformed pupe were transssected and dissociated to single cells. The cells were incubated in buffer with 40 μmolar CCF2/btAMac₂ (compound 34) for 20minutes, washed and viewed with an epifluorescence microscope (excitation filter 400DF15, emission filter 435 nm long pass). Omatidia cells from flyes transformed with the β-lactamase gene in the proper orientation fluoresced blue, while omatidia cells containing the gene in the wrong orientation fluoresced green.

Publications

Articles

G. Friedrich, P. Soriano, Methods in Enzymology, Vol. 225: 681 (1993)
G. Friedrich, P. Soriano, Genes & Development, Vol. 5: 1513 (1991)
A. Gossler, et al., Reports, 28 April: 463 (1989)
D. Hill, W. Wurst, Methods in Enzymology, Vol. 225: 664 (1993)
P. Mountford, A. Smith, TIG, Vol. 11 No. 5: 179 (1995)
P. Mountford, et al., Proc. Natl. Acad. Sci, U.S.A., Vol. 91: 4303 (1994)
Q. Niwa, et al., J. Biochem, Vol. 13: 343 (1993)
R. Reddy, et al., Proc. Natl. Acad. Sci. U.S.A., Vol. 89: 6721 (1992)
S. Shapiro, P. Senapathy, Nucleic Acids Research, Vol. 17, No. 17: 7155 (1987)
T. Skarnes, et al., Genes & Development, Vol. 6: 903 (1992)
W. Wurst, et al., Genetics, Vol. 139: 889 (1995)

All publications, including patent documents and scientific articles, referred to in this application are incorporated by reference in their entirety for all purposes to the same extent as if each individual publication were individually incorporated by reference.

All headings are for the convenience of the reader and should not be used to limit the meaning of the text that follows the heading, unless so specified.

I claim:

1. A method for identifying a function of an exogenous protein that directly or indirectly modulates a genomic polynucleotide, comprising:
   a) providing at least one living non-yeast, eukaryotic cell comprising a beta-lactamase polynucleotide that is under transcriptional control of said at least one living non-yeast, eukaryotic cell's genome and said beta-lactamase polynucleotide was stably integrated into an existing genomic polynucleotide site with a vector for random integration into said genome,
   b) contacting said at least one non-yeast, eukaryotic cell with a predetermined concentration of a known modulator, and
   c) detecting beta-lactamase activity in said at least one living non-yeast, eukaryotic cell;
   wherein said at least one living non-yeast, eukaryotic cell expresses an exogenous protein and said known modulator increases or decreases the expression of said beta-lactamase polynucleotide in the presence of said exogenous protein, further wherein said beta-lactamase polynucleotide is located in said genome and is operably linked to a control sequence of said at least one non-yeast, eukaryotic cell,
   thereby identifying a function of an expressed protein that directly or indirectly modulates a genomic polynucleotide with said known modulator.

2. The method of claim 1,
wherein said at least one living non-yeast, eukaryotic cell comprises at least one clone of a cell sorted by FACS for expression of a beta-lactamase.

3. The method of claim 1,
wherein said detecting further comprises measuring cleavage of a membrane permeant beta-lactamase substrate,
wherein said membrane permeant beta-lactamase substrate is altered in said at least one living non-yeast, eukaryotic cell into a cell membrane impermeant substrate.

4. The method of claim 3,
wherein said membrane permeant beta-lactamase substrate has a fluorescent donor moiety and a fluorescent acceptor moiety.

5. The method of claim 1,
wherein said method further comprises sorting a population of cells with a FACS.

6. The method of claim 1,
wherein said cell is a mammalian cell.

7. The method of claim 6,
wherein said beta-lactamase polynucleotide includes a beta-lactamase expression construct for random integration into said genome.

8. The method of claim 7,
further comprising the step of determining a portion of the coding nucleic acid sequence of a polynucleotide operably linked to said beta-lactamase expression construct.

9. The method of claim 6,
wherein said beta-lactamase expression construct comprises a polynucleotide encoding cytosolic beta-lactamase, a splice donor, a splice acceptor and an IRES element and said cell comprises a receptor that is known to bind said known modulator.

10. The method of claim 6,
wherein said exogenous protein is selected from the group consisting of hormone receptors, intracellular receptors, receptors of the cytokine superfamily, G-protein coupled receptors, heterologous G-proteins, neurotransmitter receptors, tyrosine kinase receptors, kinases, and transcription factors.

11. The method of claim 6,
wherein said exogenous protein has a transmembrane domain.

12. The method of claim 11,
further comprising constitutively expressing said exogenous protein.

13. The method of claim 6,
wherein said exogenous protein is under inducible control.

14. The method of claim 6,
wherein said at least one living non-yeast, eukaryotic cell is contacted with a predetermined concentration of a second modulator before said detecting step and beta-lactamase activity is detected after contacting said at least one non-yeast, eukaryotic cell with said known modulator.

15. The method of claim 6,
wherein said exogenous protein is of unknown function.

16. The method of claim 6,
wherein said beta-lactamase activity is increased in the presence of said known modulator compared to the absence of said known modulator.

17. The method of claim 6,
wherein said known modulator is known to bind to a receptor and said beta-lactamase activity in said at least one living non-yeast, eukaryotic cell is increased in the presence of said modulator compared to the beta-lactamase activity detected from a corresponding cell in the presence of said known modulator,
wherein said corresponding cell does not express said exogenous protein.

18. A method for identifying modulators, comprising:
a) contacting at least one living mammalian cell with a predetermined concentration of a test compound and a predetermined concentration of known modulator,
   wherein said at least one living mammalian cell comprises a beta-lactamase polynucleotide that is under transcriptional control of said at least one living mammalian cell's genome and is stably integrated into a genomic polynucleotide site using a vector for random integration into said genome,
   further wherein said beta-lactamase polynucleotide is located in said genome and is operably linked to a control sequence of said at least one living mammalian cell, and
b) detecting expression of said beta-lactamase polynucleotide by said at least one living mammalian cell,
   wherein said known modulator increases or decreases expression of said beta-lactamase polynucleotide located at said genomic polynucleotide site, thereby identifying a modulator that directly or indirectly modulates a genomic polynucleotide.

19. The method of claim 18,
wherein said at least one living non-yeast, eukaryotic cell comprises at least one clone of a cell sorted by FACS for expression of a beta-lactamase.

20. The method of claim 18,
wherein said test compound changes expression of said beta-lactamase polynucleotide by said known modulator and wherein said genomic polynucleotide site is part of a gene not known to be modulated by said known modulator.

21. The method of claim 18, wherein said beta-lactamase polynucleotide further comprises a splice acceptor site.

22. The method of claim 21, wherein said beta-lactamase polynucleotide further comprises an IRES.

23. The method of claim 20, wherein said test compound or known modulator is provided at a concentration less than about 1 micromolar.

24. The method of claim 18, further comprising separating a population of living mammalian cells into
   1) a population of living mammalian cells that expresses beta-lactamase, and
   2) a population of living mammalian cells that does not express beta-lactamase.

25. The method of claim 24, wherein said separating further comprises measuring cleavage of a membrane permeant beta-lactamase substrate in said population of living mammalian cells by fluorescence spectroscopy in a FACS, wherein the fluorescence of said membrane permeant beta-lactamase substrate is altered by beta-lactamase in at least one living mammalian cell into a cell membrane impermeant substrate.

26. The method of claim 18, wherein said known modulator modulates a receptor selected from the group consisting of intracellular receptors and G-protein coupled receptors.

27. The method of claim 26, wherein said known modulator is an agonist.

28. The method of claim 26, wherein said known modulator is an antagonist.

29. The method of claim 27, wherein said known modulator is contacted with said at least one living mammalian cell prior to contacting said test compound with said at least one living mammalian cell.

30. The method of claim 18, wherein said test compound is a putative modulator for a protein selected from the group consisting of hormone receptors, intracellular receptors, receptors of the cytokine superfamily, G-protein coupled receptors, heterologous G-proteins, neurotransmitter receptors, and tyrosine kinase receptors.

31. The method of claim 18, wherein said at least one living mammalian cell further comprises an exogenous protein selected from the group consisting of hormone receptors, intracellular receptors, signaling molecules, receptors of the cytokine superfamily, G-protein coupled receptors, heterologous G-proteins, neurotransmitters, and tyrosine kinase receptors.

32. The method of claim 31, wherein said exogenous protein is a G-protein coupled receptor or a heterologous G-protein.

33. The method of claim 18, further comprising the step of activating said at least one living mammalian cell with a G-protein coupled receptor modulator.

34. The method of claim 33, wherein said at least one living mammalian cell further comprises an orphan receptor.

35. The method of claim 18, wherein said at least one living mammalian cell is of cell type from a panel of different cell types and steps (a) and (b) are performed on each cell type.

36. The method of claim 18, wherein said genomic polynucleotide site is part of a gene not known to be modulated by said known modulator.

37. The method of claim 36, wherein said known modulator is as an agonist.

38. The method of claim 37, wherein said test compound is an antagonist.

39. The method of claim 36, wherein said known modulator is an antagonist.

40. The method of claim 39, wherein said test compound is an agonist.

41. A method for identifying a modulator, comprising:
a) contacting a population of non-yeast, eukaryotic cells with a predetermined concentration of a test compound and a known modulator,
   wherein a plurality of cells in said population of non-yeast, eukaryotic cells each comprise a genome with a stably integrated beta-lactamase expression construct and is under trasncriptional control of said genome with a vector for random integration into said genome,
   further wherein said beta-lactamase construct comprises:
      1) a polynucleotide encoding a protein having beta-lactamase activity, and
      2) a splice acceptor site; and
b) detecting the activity of said beta-lactamase polynucleotide expressed by said population of non-yeast, eukaryotic cells,
   wherein said known modulator increases or decreases the expression of said polynucleotide encoding a protein having beta-lactamase activity, and said known modulator modulates a biological process or target,
   further wherein said beta-lactamase polynucleotide is located in said genome and is operably linked to a control sequence of said at least one non-yeast, eukaryotic cell,
   thereby identifying a modulator that directly or indirectly modulates a genomic polynucleotide.

42. The method of claim 41, wherein said beta-lactamase expression construct further comprises a splice donor site.

43. The method of claim 42, wherein said beta-lactamase expression construct further comprises an IRES element.

44. The method of claim 41, wherein said population of non-yeast, eukaryotic cells are mammalian cells and further comprises an exogenous G-protein coupled receptor.

45. The method of claim 41, wherein said population of non-yeast, eukaryotic cells further comprises an orphan G-protein coupled receptor.

* * * * *